United States Patent
Nguyen et al.

(10) Patent No.: US 8,235,054 B2
(45) Date of Patent: *Aug. 7, 2012

(54) WOUND RETRACTOR

(75) Inventors: Eric Nguyen, Lake Elsinore, CA (US);
Donald L. Gadberry, Capistrano Beach, CA (US); Gary M. Johnson, Mission Viejo, CA (US); Charles C. Hart, Summerville, SC (US); John R. Brustad, Dana Point, CA (US); Robert R. Bowes, Laguna Hills, CA (US); Jeremy J. Albrecht, Rancho Santa Margarita, CA (US); Ghassan Sakakine, Rancho Santa Margarita, CA (US); Henry Kahle, Trabuco Canyon, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/031,892

(22) Filed: Feb. 22, 2011

(65) Prior Publication Data

US 2011/0144446 A1 Jun. 16, 2011

Related U.S. Application Data

(63) Continuation of application No. 12/693,242, filed on Jan. 25, 2010, now Pat. No. 7,913,697, which is a continuation of application No. 10/516,198, filed as application No. PCT/US03/17389 on Jun. 3, 2003, now Pat. No. 7,650,887.

(60) Provisional application No. 60/386,159, filed on Jun. 5, 2002, provisional application No. 60/415,351, filed on Oct. 2, 2002.

(51) Int. Cl.
*A61F 13/00* (2006.01)
(52) U.S. Cl. .......................................... 128/888; 128/889
(58) Field of Classification Search .................. 128/845, 128/846, 888, 889; 602/42–43, 50, 63, 75
See application file for complete search history.

(56) References Cited

U.S. PATENT DOCUMENTS

| 558,364 | A | 4/1896 | Doolittle |
| 1,157,202 | A | 10/1915 | Bates et al. |
| 1,598,284 | A | 8/1926 | Kinney |
| 1,690,995 | A | 11/1928 | Pratt |

(Continued)

FOREIGN PATENT DOCUMENTS

DE 26 05 148 A1 8/1977

(Continued)

OTHER PUBLICATIONS

US 5,344,646, Chen (withdrawn).

(Continued)

*Primary Examiner* — Michael A. Brown
(74) *Attorney, Agent, or Firm* — Cynthia A. Bonner

(57) ABSTRACT

An incrementally adjustable wound retractor (100), having a first ring (102) with a diameter greater than the desired diameter of the wound incision. A second ring (104), having an annular axis and a diameter greater than the desired diameter of the wound incision. A flexible sleeve (106), disposed in a generally cylindrical form between the first and second rings (102, 104), the second ring may be rolled over itself and around the annular axis to provide a sleeve with a radical retraction force sufficient to stretch the incision to the desired diameter.

20 Claims, 32 Drawing Sheets

U.S. PATENT DOCUMENTS

| | | |
|---|---|---|
| 1,180,466 A | 6/1931 | Deutsch |
| 1,810,466 A | 6/1931 | Deutsch |
| 2,219,564 A | 10/1940 | Reyniers |
| 2,305,289 A | 12/1942 | Coburg |
| 2,478,586 A | 8/1949 | Krapp |
| 2,669,991 A | 2/1954 | Curutchet |
| 2,695,608 A | 11/1954 | Gibbon |
| 2,812,758 A | 11/1957 | Blumenschein |
| 2,835,253 A | 5/1958 | Borgeson |
| 2,853,075 A | 9/1958 | Hoffman et al. |
| 3,039,468 A | 6/1962 | Price |
| 3,057,350 A | 10/1962 | Cowley |
| 3,111,943 A | 11/1963 | Orndorff |
| 3,195,934 A | 7/1965 | Parrish |
| 3,244,169 A | 4/1966 | Baxter |
| 3,253,594 A | 5/1966 | Matthews et al. |
| 3,313,299 A | 4/1967 | Spademan |
| 3,329,390 A | 7/1967 | Hulsey |
| 3,332,417 A | 7/1967 | Blanford et al. |
| 3,347,226 A | 10/1967 | Harrower |
| 3,347,227 A | 10/1967 | Harrower |
| 3,397,692 A | 8/1968 | Creager, Jr. et al. |
| 3,402,710 A | 9/1968 | Paleschuck |
| 3,416,520 A | 12/1968 | Creager, Jr. |
| 3,447,533 A | 6/1969 | Spicer |
| 3,522,800 A | 8/1970 | Lesser |
| 3,523,534 A | 8/1970 | Nolan |
| 3,570,475 A | 3/1971 | Weinstein |
| 3,656,485 A | 4/1972 | Robertson |
| 3,685,786 A | 8/1972 | Woodson |
| 3,717,151 A | 2/1973 | Collett |
| 3,717,883 A | 2/1973 | Mosher |
| 3,729,006 A | 4/1973 | Wilder et al. |
| 3,782,370 A | 1/1974 | McDonald |
| 3,797,478 A | 3/1974 | Walsh et al. |
| 3,799,166 A | 3/1974 | Marsan |
| 3,807,393 A | 4/1974 | McDonald |
| 3,828,764 A | 8/1974 | Jones |
| 3,831,583 A | 8/1974 | Edmunds et al. |
| 3,841,332 A | 10/1974 | Treacle |
| 3,850,172 A | 11/1974 | Cazalis |
| 3,853,126 A | 12/1974 | Schulte |
| 3,853,127 A | 12/1974 | Spademan |
| 3,856,021 A | 12/1974 | McIntosh |
| 3,860,274 A | 1/1975 | Ledstrom et al. |
| 3,861,416 A | 1/1975 | Wichterle |
| 3,907,389 A | 9/1975 | Cox et al. |
| 3,915,171 A | 10/1975 | Shermeta |
| 3,965,890 A | 6/1976 | Gauthier |
| 3,970,089 A | 7/1976 | Saice |
| 3,996,623 A | 12/1976 | Kaster |
| 4,000,739 A | 1/1977 | Stevens |
| 4,016,884 A | 4/1977 | Kwan-Gett |
| 4,024,872 A | 5/1977 | Muldoon |
| 4,030,500 A | 6/1977 | Ronnquist |
| 4,043,328 A | 8/1977 | Cawood, Jr. et al. |
| 4,069,913 A | 1/1978 | Harrigan |
| 4,082,005 A | 4/1978 | Erdley |
| 4,083,370 A | 4/1978 | Taylor |
| 4,096,853 A | 6/1978 | Weigand |
| 4,112,932 A | 9/1978 | Chiulli |
| 4,130,113 A | 12/1978 | Graham |
| 4,177,814 A | 12/1979 | Knepshield et al. |
| 4,183,357 A | 1/1980 | Bentley et al. |
| 4,187,849 A | 2/1980 | Stim |
| 4,188,945 A | 2/1980 | Wenander |
| 4,217,664 A | 8/1980 | Faso |
| 4,222,126 A | 9/1980 | Boretos et al. |
| 4,228,792 A | 10/1980 | Rhys-Davies |
| 4,239,036 A | 12/1980 | Krieger |
| 4,240,411 A | 12/1980 | Hosono |
| 4,253,201 A | 3/1981 | Ross et al. |
| 4,254,973 A | 3/1981 | Benjamin |
| 4,306,562 A | 12/1981 | Osborne |
| 4,321,915 A | 3/1982 | Leighton |
| 4,331,138 A | 5/1982 | Jessen |
| 4,338,934 A | 7/1982 | Spademan |
| 4,338,937 A | 7/1982 | Lerman |
| 4,367,728 A | 1/1983 | Mutke |
| 4,369,284 A | 1/1983 | Chen |
| 4,399,816 A | 8/1983 | Spangler |
| 4,402,683 A | 9/1983 | Kopman |
| 4,411,659 A | 10/1983 | Jensen et al. |
| 4,421,296 A | 12/1983 | Stephens |
| 4,424,833 A | 1/1984 | Spector et al. |
| 4,428,364 A | 1/1984 | Bartolo |
| 4,430,081 A | 2/1984 | Timmermans |
| 4,434,791 A | 3/1984 | Darnell |
| 4,436,519 A | 3/1984 | O'Neill |
| 4,454,873 A | 6/1984 | Laufenberg et al. |
| 4,473,067 A | 9/1984 | Schiff |
| 4,475,548 A | 10/1984 | Muto |
| 4,485,490 A | 12/1984 | Akers et al. |
| 4,488,877 A | 12/1984 | Klein |
| 4,543,088 A | 9/1985 | Bootman et al. |
| 4,550,713 A | 11/1985 | Hyman |
| 4,553,537 A | 11/1985 | Rosenberg |
| 4,555,242 A | 11/1985 | Saudagar |
| 4,556,996 A | 12/1985 | Wallace |
| 4,601,710 A | 7/1986 | Moll |
| 4,610,665 A | 9/1986 | Matsumoto et al. |
| 4,626,245 A | 12/1986 | Weinstein |
| 4,634,424 A | 1/1987 | O'Boyle |
| 4,634,432 A | 1/1987 | Kocak |
| 4,644,951 A | 2/1987 | Bays |
| 4,649,904 A | 3/1987 | Krauter |
| 4,653,476 A | 3/1987 | Bonnet |
| 4,654,030 A | 3/1987 | Moll et al. |
| 4,655,752 A | 4/1987 | Honkanen et al. |
| 4,673,393 A | 6/1987 | Suzuki et al. |
| 4,673,394 A | 6/1987 | Fenton |
| 4,691,942 A | 9/1987 | Ford |
| 4,714,749 A | 12/1987 | Hughes et al. |
| 4,738,666 A | 4/1988 | Fuqua |
| 4,755,170 A | 7/1988 | Golden |
| 4,760,933 A | 8/1988 | Christner et al. |
| 4,776,843 A | 10/1988 | Martinez et al. |
| 4,777,943 A | 10/1988 | Chvapil |
| 4,784,646 A | 11/1988 | Feingold |
| 4,796,629 A | 1/1989 | Grayzel |
| 4,798,594 A | 1/1989 | Hillstead |
| 4,802,694 A | 2/1989 | Vargo |
| 4,808,168 A | 2/1989 | Warring |
| 4,809,679 A | 3/1989 | Shimonaka et al. |
| 4,828,554 A | 5/1989 | Griffin |
| 4,842,931 A | 6/1989 | Zook |
| 4,848,575 A | 7/1989 | Nakamura et al. |
| 4,856,502 A | 8/1989 | Ersfeld et al. |
| 4,863,430 A | 9/1989 | Klyce et al. |
| 4,863,438 A | 9/1989 | Gauderer et al. |
| 4,889,107 A | 12/1989 | Kaufman |
| 4,895,565 A | 1/1990 | Hillstead |
| 4,897,081 A | 1/1990 | Poirier |
| 4,903,710 A | 2/1990 | Jessamine et al. |
| 4,911,974 A | 3/1990 | Shimizu et al. |
| 4,915,132 A | 4/1990 | Hodge et al. |
| 4,926,882 A | 5/1990 | Lawrence |
| 4,929,235 A | 5/1990 | Merry et al. |
| 4,944,732 A | 7/1990 | Russo |
| 4,950,222 A | 8/1990 | Scott et al. |
| 4,950,223 A | 8/1990 | Silvanov |
| 4,984,564 A | 1/1991 | Yuen |
| 4,991,593 A | 2/1991 | LeVahn |
| 4,998,538 A | 3/1991 | Charowsky et al. |
| 5,000,745 A | 3/1991 | Guest et al. |
| 5,009,224 A | 4/1991 | Cole |
| 5,015,228 A | 5/1991 | Columbus et al. |
| 5,019,101 A | 5/1991 | Purkait et al. |
| 5,026,366 A | 6/1991 | Leckrone |
| 5,037,379 A | 8/1991 | Clayman et al. |
| 5,041,095 A | 8/1991 | Littrell |
| 5,045,070 A | 9/1991 | Grodecki et al. |
| D320,658 S | 10/1991 | Quigley et al. |
| 5,071,411 A | 12/1991 | Hillstead |
| 5,073,169 A | 12/1991 | Raiken |
| 5,074,878 A | 12/1991 | Bark et al. |
| 5,082,005 A | 1/1992 | Kaldany |

| | | | | | | |
|---|---|---|---|---|---|---|
| 5,086,763 A | 2/1992 | Hathman | | 5,366,446 A | 11/1994 | Tal et al. |
| 5,092,846 A | 3/1992 | Nishijima et al. | | 5,366,478 A | 11/1994 | Brinkerhoff et al. |
| 5,104,389 A | 4/1992 | Deem | | 5,368,545 A | 11/1994 | Schaller et al. |
| 5,125,396 A | 6/1992 | Ray | | 5,375,588 A | 12/1994 | Yoon |
| 5,125,897 A | 6/1992 | Quinn et al. | | 5,380,288 A | 1/1995 | Hart et al. |
| 5,127,626 A | 7/1992 | Hilal et al. | | 5,383,861 A | 1/1995 | Hempel et al. |
| 5,129,885 A | 7/1992 | Green et al. | | 5,385,552 A | 1/1995 | Haber et al. |
| 5,141,498 A | 8/1992 | Christian | | 5,385,553 A | 1/1995 | Hart et al. |
| 5,149,327 A | 9/1992 | Oshiyama | | 5,385,560 A | 1/1995 | Wulf |
| 5,156,617 A | 10/1992 | Reid | | 5,389,080 A | 2/1995 | Yoon |
| 5,158,553 A | 10/1992 | Berry et al. | | 5,389,081 A | 2/1995 | Castro |
| 5,159,921 A | 11/1992 | Hoover | | 5,391,153 A | 2/1995 | Haber et al. |
| 5,161,773 A | 11/1992 | Tower | | 5,391,156 A | 2/1995 | Hildwein et al. |
| 5,167,636 A | 12/1992 | Clement | | 5,395,367 A | 3/1995 | Wilk |
| 5,167,637 A | 12/1992 | Okada et al. | | 5,403,264 A | 4/1995 | Wohlers et al. |
| 5,176,648 A | 1/1993 | Holmes et al. | | 5,403,336 A | 4/1995 | Kieturakis et al. |
| 5,176,662 A | 1/1993 | Bartholomew et al. | | 5,407,433 A | 4/1995 | Loomas |
| 5,176,697 A | 1/1993 | Hasson et al. | | 5,411,483 A | 5/1995 | Loomas |
| 5,178,162 A | 1/1993 | Bose | | 5,413,571 A | 5/1995 | Katsaros et al. |
| 5,180,365 A | 1/1993 | Ensminger et al. | | 5,423,848 A | 6/1995 | Washizuka et al. |
| 5,183,471 A | 2/1993 | Wilk | | 5,429,609 A | 7/1995 | Yoon |
| 5,188,595 A | 2/1993 | Jacobi | | 5,431,676 A | 7/1995 | Dubrul et al. |
| 5,188,607 A | 2/1993 | Wu | | 5,437,683 A | 8/1995 | Neumann et al. |
| 5,192,301 A | 3/1993 | Kamiya et al. | | 5,439,455 A | 8/1995 | Kieturakis et al. |
| 5,197,955 A | 3/1993 | Stephens et al. | | 5,441,486 A | 8/1995 | Yoon |
| 5,207,656 A | 5/1993 | Kranys | | 5,443,452 A | 8/1995 | Hart et al. |
| 5,209,737 A | 5/1993 | Ritchart et al. | | 5,456,284 A | 10/1995 | Ryan et al. |
| 5,211,370 A | 5/1993 | Powers | | 5,460,170 A | 10/1995 | Hammerslag |
| 5,211,633 A | 5/1993 | Stouder, Jr. | | 5,460,616 A | 10/1995 | Weinstein et al. |
| 5,213,114 A | 5/1993 | Bailey, Jr. | | 5,468,248 A | 11/1995 | Chin et al. |
| 5,226,890 A | 7/1993 | Ianniruberto et al. | | 5,476,475 A | 12/1995 | Gadberry |
| 5,234,455 A | 8/1993 | Mulhollan | | 5,480,410 A | 1/1996 | Cuschieri et al. |
| 5,241,968 A | 9/1993 | Slater | | 5,486,426 A | 1/1996 | McGee et al. |
| 5,242,409 A | 9/1993 | Buelna | | 5,490,843 A | 2/1996 | Hildwein et al. |
| 5,242,412 A | 9/1993 | Blake, III | | 5,492,304 A | 2/1996 | Smith et al. |
| 5,242,415 A | 9/1993 | Kantrowitz et al. | | 5,496,280 A | 3/1996 | Vandenbroek et al. |
| 5,242,459 A | 9/1993 | Buelna | | 5,503,112 A | 4/1996 | Luhman et al. |
| 5,248,304 A | 9/1993 | Vigdorchik et al. | | 5,507,758 A | 4/1996 | Thomason et al. |
| 5,256,150 A | 10/1993 | Quiachon et al. | | 5,508,334 A | 4/1996 | Chen |
| 5,257,973 A | 11/1993 | Villasuso | | 5,511,564 A | 4/1996 | Wilk |
| 5,257,975 A | 11/1993 | Foshee | | 5,514,109 A | 5/1996 | Mollenauer et al. |
| 5,259,366 A | 11/1993 | Reydel et al. | | 5,514,133 A | 5/1996 | Golub et al. |
| 5,261,883 A | 11/1993 | Hood et al. | | 5,514,153 A | 5/1996 | Bonutti |
| 5,262,468 A | 11/1993 | Chen | | 5,518,278 A | 5/1996 | Sampson |
| 5,263,922 A | 11/1993 | Sova et al. | | 5,520,632 A | 5/1996 | Leveen |
| 5,269,763 A | 12/1993 | Boehmer et al. | | 5,522,791 A | 6/1996 | Leyva |
| 5,269,772 A | 12/1993 | Wilk | | 5,522,824 A | 6/1996 | Ashby |
| 5,273,449 A | 12/1993 | Mattis et al. | | 5,524,644 A * | 6/1996 | Crook ............................. 128/888 |
| 5,273,545 A | 12/1993 | Hunt et al. | | 5,526,536 A | 6/1996 | Cartmill |
| D343,236 S | 1/1994 | Quigley et al. | | 5,531,758 A | 7/1996 | Uschold et al. |
| 5,279,575 A | 1/1994 | Sugarbaker | | 5,538,509 A | 7/1996 | Dunlap et al. |
| 5,290,310 A | 3/1994 | Makower et al. | | 5,540,648 A | 7/1996 | Yoon |
| D346,022 S | 4/1994 | Quigley et al. | | 5,540,711 A | 7/1996 | Kieturakis et al. |
| 5,299,582 A | 4/1994 | Potts | | 5,545,150 A | 8/1996 | Danks et al. |
| 5,300,034 A | 4/1994 | Behnke | | 5,545,179 A | 8/1996 | Williamson, IV |
| 5,300,035 A | 4/1994 | Clement | | 5,549,563 A | 8/1996 | Kronner |
| 5,300,036 A | 4/1994 | Mueller et al. | | 5,549,637 A | 8/1996 | Crainich |
| 5,308,336 A | 5/1994 | Hart et al. | | 5,554,124 A | 9/1996 | Alvarado |
| 5,309,896 A | 5/1994 | Moll et al. | | 5,562,632 A | 10/1996 | Davila et al. |
| 5,312,391 A | 5/1994 | Wilk | | 5,562,677 A | 10/1996 | Hildwein et al. |
| 5,314,417 A | 5/1994 | Stephens et al. | | 5,562,688 A | 10/1996 | Riza |
| 5,316,541 A | 5/1994 | Fischer | | 5,571,115 A | 11/1996 | Nicholas |
| 5,320,611 A | 6/1994 | Bonutti et al. | | 5,571,137 A | 11/1996 | Marlow et al. |
| 5,330,437 A | 7/1994 | Durman | | 5,575,799 A | 11/1996 | Bolanos et al. |
| 5,330,486 A | 7/1994 | Wilk | | 5,577,993 A | 11/1996 | Zhu et al. |
| 5,330,497 A | 7/1994 | Freitas et al. | | 5,578,048 A | 11/1996 | Pasqualucci et al. |
| 5,331,975 A | 7/1994 | Bonutti | | 5,580,344 A | 12/1996 | Hasson |
| 5,334,143 A | 8/1994 | Carroll | | 5,584,850 A | 12/1996 | Hart et al. |
| 5,336,192 A | 8/1994 | Palestrant | | 5,601,579 A | 2/1997 | Semertzides |
| 5,336,708 A | 8/1994 | Chen | | 5,601,581 A | 2/1997 | Fogarty et al. |
| 5,338,313 A | 8/1994 | Mollenauer et al. | | 5,603,702 A | 2/1997 | Smith et al. |
| 5,342,315 A | 8/1994 | Rowe et al. | | 5,607,443 A | 3/1997 | Kieturakis et al. |
| 5,342,385 A | 8/1994 | Norelli et al. | | 5,620,415 A | 4/1997 | Lucey et al. |
| 5,350,364 A | 9/1994 | Stephens et al. | | 5,620,420 A | 4/1997 | Kriesel |
| 5,353,786 A | 10/1994 | Wilk | | 5,628,732 A | 5/1997 | Antoon, Jr. et al. |
| 5,354,280 A | 10/1994 | Haber et al. | | 5,632,284 A | 5/1997 | Graether |
| 5,360,417 A | 11/1994 | Gravener et al. | | 5,632,979 A | 5/1997 | Goldberg et al. |
| 5,364,345 A | 11/1994 | Lowery et al. | | 5,634,911 A | 6/1997 | Hermann et al. |
| 5,364,372 A | 11/1994 | Danks et al. | | 5,634,936 A | 6/1997 | Linden et al. |

| | | | | | |
|---|---|---|---|---|---|
| 5,634,937 A | 6/1997 | Mollenauer et al. | 5,916,198 A | 6/1999 | Dillow |
| 5,636,645 A | 6/1997 | Ou | 5,916,232 A | 6/1999 | Hart |
| 5,640,977 A | 6/1997 | Leahy et al. | 5,919,476 A | 7/1999 | Fischer et al. |
| 5,643,301 A | 7/1997 | Mollenauer | 5,931,832 A | 8/1999 | Jensen |
| 5,649,550 A | 7/1997 | Crook | 5,947,922 A | 9/1999 | MacLeod |
| 5,651,771 A | 7/1997 | Tangherlini et al. | 5,951,467 A | 9/1999 | Picha et al. |
| 5,653,705 A | 8/1997 | de la Torre et al. | 5,951,588 A | 9/1999 | Moenning |
| 5,657,963 A | 8/1997 | Hinchliffe et al. | 5,957,888 A | 9/1999 | Hinchliffe |
| 5,658,272 A | 8/1997 | Hasson | 5,957,913 A | 9/1999 | de la Torre et al. |
| 5,658,306 A | 8/1997 | Kieturakis et al. | 5,962,572 A | 10/1999 | Chen |
| 5,662,615 A | 9/1997 | Blake, III | 5,964,781 A | 10/1999 | Mollenauer et al. |
| 5,672,168 A | 9/1997 | de la Torre et al. | 5,976,174 A | 11/1999 | Ruiz |
| 5,681,341 A | 10/1997 | Lunsford et al. | 5,989,232 A | 11/1999 | Yoon |
| 5,683,378 A | 11/1997 | Christy | 5,989,233 A | 11/1999 | Yoon |
| 5,685,854 A | 11/1997 | Green et al. | 5,989,266 A | 11/1999 | Foster |
| 5,685,857 A | 11/1997 | Negus et al. | 5,993,471 A | 11/1999 | Riza et al. |
| 5,697,914 A | 12/1997 | Brimhall | 5,993,485 A | 11/1999 | Beckers |
| 5,707,703 A | 1/1998 | Rothrum et al. | 5,994,450 A | 11/1999 | Pearce |
| 5,709,664 A | 1/1998 | Vandenbroek et al. | 5,997,515 A | 12/1999 | de la Torre et al. |
| 5,713,858 A | 2/1998 | Heruth et al. | 6,004,303 A | 12/1999 | Peterson |
| 5,713,869 A | 2/1998 | Morejon | 6,010,494 A | 1/2000 | Schafer et al. |
| 5,720,730 A | 2/1998 | Blake, III | 6,017,355 A | 1/2000 | Hessel et al. |
| 5,725,536 A | 3/1998 | Oberlin et al. | 6,018,094 A | 1/2000 | Fox |
| 5,728,103 A | 3/1998 | Picha et al. | 6,024,736 A | 2/2000 | de la Torre et al. |
| 5,730,748 A | 3/1998 | Fogarty et al. | 6,025,067 A | 2/2000 | Fay |
| 5,735,791 A | 4/1998 | Alexander et al. | 6,033,426 A | 3/2000 | Kaji |
| 5,738,628 A | 4/1998 | Sierocuk et al. | 6,033,428 A | 3/2000 | Sardella |
| 5,741,234 A | 4/1998 | Aboul-Hosn | 6,035,559 A | 3/2000 | Freed et al. |
| 5,741,298 A | 4/1998 | MacLeod | 6,042,573 A | 3/2000 | Lucey |
| 5,743,884 A | 4/1998 | Hasson et al. | 6,045,535 A | 4/2000 | Ben Nun |
| 5,749,882 A | 5/1998 | Hart et al. | 6,048,309 A | 4/2000 | Flom et al. |
| 5,753,150 A | 5/1998 | Martin et al. | 6,050,871 A | 4/2000 | Chen |
| 5,755,660 A | 5/1998 | Tyagi | 6,053,934 A | 4/2000 | Andrews et al. |
| 5,760,117 A | 6/1998 | Chen | 6,059,806 A | 5/2000 | Moenning |
| 5,769,783 A | 6/1998 | Fowler | 6,066,117 A | 5/2000 | Fox et al. |
| 5,782,812 A | 7/1998 | Hart et al. | 6,068,639 A | 5/2000 | Fogarty et al. |
| 5,782,817 A | 7/1998 | Franzel et al. | 6,077,288 A | 6/2000 | Shimomura |
| 5,782,859 A | 7/1998 | Nicholas et al. | 6,086,603 A | 7/2000 | Termin et al. |
| 5,788,676 A | 8/1998 | Yoon | 6,090,043 A | 7/2000 | Austin et al. |
| 5,792,119 A | 8/1998 | Marx | 6,099,506 A | 8/2000 | Macoviak et al. |
| 5,795,290 A | 8/1998 | Bridges | 6,110,154 A | 8/2000 | Shimomura et al. |
| 5,803,919 A | 9/1998 | Hart et al. | 6,123,689 A | 9/2000 | To et al. |
| 5,803,921 A | 9/1998 | Bonadio | 6,142,935 A | 11/2000 | Flom et al. |
| 5,803,923 A | 9/1998 | Singh-Derewa et al. | 6,142,936 A | 11/2000 | Beane et al. |
| 5,807,350 A | 9/1998 | Diaz | 6,149,642 A | 11/2000 | Gerhart et al. |
| 5,810,712 A | 9/1998 | Dunn | 6,150,608 A | 11/2000 | Wambeke et al. |
| 5,810,721 A | 9/1998 | Mueller et al. | 6,159,182 A | 12/2000 | Davis |
| 5,813,409 A | 9/1998 | Leahy et al. | 6,162,172 A | 12/2000 | Cosgrove et al. |
| 5,814,026 A | 9/1998 | Yoon | 6,162,196 A | 12/2000 | Hart et al. |
| 5,817,062 A | 10/1998 | Flom et al. | 6,162,206 A | 12/2000 | Bindokas |
| 5,819,375 A | 10/1998 | Kastner | 6,163,949 A | 12/2000 | Neuenschwander |
| 5,820,555 A | 10/1998 | Watkins, III et al. | 6,164,279 A | 12/2000 | Tweedle |
| 5,820,600 A | 10/1998 | Carlson et al. | 6,171,282 B1 | 1/2001 | Ragsdale |
| 5,830,191 A | 11/1998 | Hildwein et al. | 6,183,486 B1 | 2/2001 | Snow et al. |
| 5,832,925 A | 11/1998 | Rothrum | 6,197,002 B1 | 3/2001 | Peterson |
| 5,836,871 A | 11/1998 | Wallace et al. | 6,217,555 B1 | 4/2001 | Hart et al. |
| 5,841,298 A | 11/1998 | Huang | 6,217,590 B1 | 4/2001 | Levinson |
| 5,842,971 A | 12/1998 | Yoon | 6,224,612 B1 | 5/2001 | Bates et al. |
| 5,848,992 A | 12/1998 | Hart et al. | 6,228,063 B1 | 5/2001 | Aboul-Hosn |
| 5,853,395 A | 12/1998 | Crook et al. | 6,238,373 B1 | 5/2001 | de la Torre et al. |
| 5,853,417 A | 12/1998 | Fogarty et al. | 6,241,768 B1 | 6/2001 | Agarwal et al. |
| 5,857,461 A | 1/1999 | Levitsky et al. | 6,254,533 B1 | 7/2001 | Fadem et al. |
| 5,860,995 A | 1/1999 | Berkelaar | 6,254,534 B1 | 7/2001 | Butler et al. |
| 5,865,728 A | 2/1999 | Moll et al. | 6,258,065 B1 | 7/2001 | Dennis et al. |
| 5,865,729 A | 2/1999 | Meehan et al. | 6,264,604 B1 | 7/2001 | Kieturakis et al. |
| 5,865,807 A | 2/1999 | Blake, III | 6,267,751 B1 | 7/2001 | Mangosong |
| 5,865,817 A | 2/1999 | Moenning et al. | 6,276,661 B1 | 8/2001 | Laird |
| 5,871,474 A | 2/1999 | Hermann et al. | 6,287,280 B1 | 9/2001 | Lampropoulos et al. |
| 5,876,413 A | 3/1999 | Fogarty et al. | 6,315,770 B1 | 11/2001 | de la Torre et al. |
| 5,879,368 A | 3/1999 | Hoskin et al. | 6,319,246 B1 | 11/2001 | de la Torre et al. |
| 5,882,344 A | 3/1999 | Stouder, Jr. | 6,322,541 B2 | 11/2001 | West |
| 5,884,639 A | 3/1999 | Chen | 6,325,384 B1 | 12/2001 | Berry, Sr. et al. |
| 5,894,843 A | 4/1999 | Benetti et al. | 6,346,074 B1 | 2/2002 | Roth |
| 5,895,377 A | 4/1999 | Smith et al. | 6,371,968 B1 | 4/2002 | Kogasaka et al. |
| 5,899,208 A | 5/1999 | Bonadio | 6,382,211 B1 | 5/2002 | Crook |
| 5,899,913 A | 5/1999 | Fogarty et al. | 6,383,162 B1 | 5/2002 | Sugarbaker |
| 5,904,703 A | 5/1999 | Gilson | 6,391,043 B1 | 5/2002 | Moll et al. |
| 5,906,577 A | 5/1999 | Beane et al. | 6,413,244 B1 | 7/2002 | Bestetti et al. |
| 5,913,847 A | 6/1999 | Yoon | 6,413,458 B1 | 7/2002 | Pearce |

| Patent No. | Date | Inventor |
|---|---|---|
| 6,420,475 B1 | 7/2002 | Chen |
| 6,423,036 B1 | 7/2002 | Van Huizen |
| 6,440,061 B1 | 8/2002 | Wenner et al. |
| 6,440,063 B1 | 8/2002 | Beane et al. |
| 6,443,957 B1 | 9/2002 | Addis |
| 6,447,489 B1 | 9/2002 | Peterson |
| 6,450,983 B1 | 9/2002 | Rambo |
| 6,454,783 B1 | 9/2002 | Piskun |
| 6,464,686 B1 | 10/2002 | O'Hara et al. |
| 6,468,292 B1 | 10/2002 | Mollenauer et al. |
| 6,482,181 B1 | 11/2002 | Racenet et al. |
| 6,485,435 B1 | 11/2002 | Bakal |
| 6,485,467 B1 | 11/2002 | Crook et al. |
| 6,488,620 B1 | 12/2002 | Segermark et al. |
| 6,488,692 B1 | 12/2002 | Spence et al. |
| 6,494,893 B2 | 12/2002 | Dubrul et al. |
| 6,527,787 B1 | 3/2003 | Fogarty et al. |
| 6,533,734 B1 | 3/2003 | Corley, III et al. |
| 6,551,270 B1 | 4/2003 | Bimbo et al. |
| 6,551,276 B1 | 4/2003 | Mann et al. |
| 6,551,344 B2 | 4/2003 | Thill |
| 6,552,109 B1 | 4/2003 | Chen |
| 6,554,793 B1 | 4/2003 | Pauker et al. |
| 6,558,371 B2 | 5/2003 | Dorn |
| 6,569,120 B1 | 5/2003 | Green |
| 6,578,577 B2 | 6/2003 | Bonadio et al. |
| 6,579,281 B2 | 6/2003 | Palmer et al. |
| 6,582,364 B2 | 6/2003 | Butler et al. |
| 6,589,167 B1 | 7/2003 | Shimomura et al. |
| 6,589,211 B1 | 7/2003 | MacLeod |
| 6,607,504 B2 | 8/2003 | Haarala et al. |
| 6,613,952 B2 | 9/2003 | Rambo |
| 6,623,426 B2 | 9/2003 | Bonadio et al. |
| 6,627,275 B1 | 9/2003 | Chen |
| 6,663,598 B1 | 12/2003 | Carrillo et al. |
| 6,669,674 B1 | 12/2003 | Macoviak et al. |
| 6,676,639 B1 | 1/2004 | Ternström |
| 6,702,787 B2 | 3/2004 | Racenet et al. |
| 6,705,989 B2 | 3/2004 | Cuschieri et al. |
| 6,706,050 B1 | 3/2004 | Giannadakis |
| 6,714,298 B2 | 3/2004 | Ryer |
| 6,716,201 B2 | 4/2004 | Blanco |
| 6,723,044 B2 | 4/2004 | Pulford et al. |
| 6,723,088 B2 | 4/2004 | Gaskill, III et al. |
| 6,725,080 B2 | 4/2004 | Melkent et al. |
| 6,793,621 B2 | 9/2004 | Butler et al. |
| 6,794,440 B2 | 9/2004 | Chen |
| 6,796,940 B2 | 9/2004 | Bonadio et al. |
| 6,797,765 B2 | 9/2004 | Pearce |
| 6,800,084 B2 | 10/2004 | Davison et al. |
| 6,811,546 B1 | 11/2004 | Callas et al. |
| 6,814,078 B2 | 11/2004 | Crook |
| 6,814,700 B1 | 11/2004 | Mueller et al. |
| 6,817,974 B2 | 11/2004 | Cooper et al. |
| 6,830,578 B2 | 12/2004 | O'Heeron et al. |
| 6,837,893 B2 | 1/2005 | Miller |
| 6,840,946 B2 | 1/2005 | Fogarty et al. |
| 6,840,951 B2 | 1/2005 | de la Torre et al. |
| 6,846,287 B2 | 1/2005 | Bonadio et al. |
| 6,860,463 B2 | 3/2005 | Hartley |
| 6,863,674 B2 | 3/2005 | Kasahara et al. |
| 6,866,861 B1 | 3/2005 | Luhman |
| 6,867,253 B1 | 3/2005 | Chen |
| 6,869,393 B2 | 3/2005 | Butler |
| 6,878,110 B2 | 4/2005 | Yang et al. |
| 6,884,253 B1 | 4/2005 | McFarlane |
| 6,890,295 B2 | 5/2005 | Michels et al. |
| 6,895,965 B2 | 5/2005 | Scarberry et al. |
| 6,902,541 B2 | 6/2005 | McNally et al. |
| 6,902,569 B2 | 6/2005 | Parmer et al. |
| 6,908,430 B2 | 6/2005 | Caldwell et al. |
| 6,909,220 B2 | 6/2005 | Chen |
| 6,913,609 B2 | 7/2005 | Yencho et al. |
| 6,916,310 B2 | 7/2005 | Sommerich |
| 6,916,331 B2 | 7/2005 | Mollenauer et al. |
| 6,929,637 B2 | 8/2005 | Gonzalez et al. |
| 6,936,037 B2 | 8/2005 | Bubb et al. |
| 6,939,296 B2 | 9/2005 | Ewers et al. |
| 6,945,932 B1 | 9/2005 | Caldwell et al. |
| 6,958,037 B2 | 10/2005 | Ewers et al. |
| 6,972,026 B1 | 12/2005 | Caldwell et al. |
| 6,979,324 B2 | 12/2005 | Bybordi et al. |
| 6,991,602 B2 | 1/2006 | Nakazawa et al. |
| 6,997,909 B2 | 2/2006 | Goldberg |
| 7,001,397 B2 | 2/2006 | Davison et al. |
| 7,008,377 B2 | 3/2006 | Beane et al. |
| 7,014,628 B2 | 3/2006 | Bousquet |
| 7,033,319 B2 | 4/2006 | Pulford et al. |
| 7,052,454 B2 | 5/2006 | Taylor |
| 7,056,304 B2 | 6/2006 | Bacher et al. |
| 7,056,321 B2 | 6/2006 | Pagliuca et al. |
| 7,067,583 B2 | 6/2006 | Chen |
| 7,077,852 B2 | 7/2006 | Fogarty et al. |
| 7,081,089 B2 | 7/2006 | Bonadio et al. |
| 7,083,626 B2 | 8/2006 | Hart et al. |
| 7,093,599 B2 | 8/2006 | Chen |
| 7,100,614 B2 | 9/2006 | Stevens et al. |
| 7,101,353 B2 | 9/2006 | Lui et al. |
| 7,105,009 B2 | 9/2006 | Johnson |
| 7,105,607 B2 | 9/2006 | Chen |
| 7,112,185 B2 | 9/2006 | Hart et al. |
| 7,118,528 B1 | 10/2006 | Piskun |
| 7,134,929 B2 | 11/2006 | Chen |
| 7,153,261 B2 | 12/2006 | Wenchell |
| 7,163,510 B2 | 1/2007 | Kahle et al. |
| 7,192,436 B2 | 3/2007 | Sing et al. |
| 7,193,002 B2 | 3/2007 | Chen |
| 7,195,590 B2 | 3/2007 | Butler et al. |
| 7,214,185 B1 | 5/2007 | Rosney et al. |
| 7,217,277 B2 | 5/2007 | Parihar et al. |
| 7,222,380 B2 | 5/2007 | Chen |
| 7,223,257 B2 | 5/2007 | Shubayev et al. |
| 7,223,278 B2 | 5/2007 | Davison et al. |
| 7,226,484 B2 | 6/2007 | Chen |
| 7,235,062 B2 | 6/2007 | Brustad |
| 7,235,084 B2 | 6/2007 | Skakoon et al. |
| 7,238,154 B2 | 7/2007 | Ewers et al. |
| 7,244,244 B2 | 7/2007 | Racenet et al. |
| 7,276,075 B1 | 10/2007 | Callas et al. |
| 7,290,367 B2 | 11/2007 | Chen |
| 7,294,103 B2 | 11/2007 | Bertolero et al. |
| 7,297,106 B2 | 11/2007 | Yamada et al. |
| 7,300,399 B2 | 11/2007 | Bonadio et al. |
| 7,316,699 B2 | 1/2008 | McFarlane |
| 7,331,940 B2 | 2/2008 | Sommerich |
| 7,338,473 B2 | 3/2008 | Campbell et al. |
| 7,344,546 B2 | 3/2008 | Piskun |
| 7,344,547 B2 | 3/2008 | Piskun |
| 7,344,568 B2 | 3/2008 | Chen |
| 7,377,898 B2 | 5/2008 | Ewers et al. |
| 7,390,317 B2 | 6/2008 | Taylor et al. |
| 7,393,322 B2 | 7/2008 | Wenchell |
| 7,412,977 B2 | 8/2008 | Fields et al. |
| 7,445,597 B2 | 11/2008 | Butler et al. |
| 7,473,221 B2 | 1/2009 | Ewers et al. |
| 7,481,765 B2 | 1/2009 | Ewers et al. |
| 7,537,564 B2 | 5/2009 | Bonadio et al. |
| 7,540,839 B2 | 6/2009 | Butler et al. |
| 7,559,893 B2 | 7/2009 | Bonadio et al. |
| 7,578,832 B2 | 8/2009 | Johnson |
| 7,645,232 B2 | 1/2010 | Shluzas |
| 7,650,887 B2 | 1/2010 | Nguyen et al. |
| 7,661,164 B2 | 2/2010 | Chen |
| 7,704,207 B2 | 4/2010 | Albrecht et al. |
| 7,717,847 B2 | 5/2010 | Smith |
| 7,727,146 B2 | 6/2010 | Albrecht et al. |
| 7,727,225 B2 | 6/2010 | Taylor et al. |
| 7,736,306 B2 | 6/2010 | Brustad et al. |
| 7,749,415 B2 | 7/2010 | Brustad et al. |
| 7,753,901 B2 | 7/2010 | Piskun et al. |
| 7,758,500 B2 | 7/2010 | Boyd et al. |
| 7,766,824 B2 | 8/2010 | Jensen et al. |
| 7,811,251 B2 | 10/2010 | Wenchell et al. |
| 7,815,567 B2 | 10/2010 | Albrecht et al. |
| 7,837,612 B2 | 11/2010 | Gill et al. |
| 7,850,667 B2 | 12/2010 | Gresham |
| 7,867,164 B2 | 1/2011 | Butler et al. |
| 7,878,974 B2 | 2/2011 | Brustad et al. |

| | | |
|---|---|---|
| 7,896,889 B2 | 3/2011 | Mazzocchi et al. |
| 7,909,760 B2 | 3/2011 | Albrecht et al. |
| 7,930,782 B2 | 4/2011 | Chen |
| 2001/0037053 A1 | 11/2001 | Bonadio et al. |
| 2001/0047188 A1 | 11/2001 | Bonadio et al. |
| 2002/0002324 A1 | 1/2002 | McManus |
| 2002/0010389 A1 | 1/2002 | Butler et al. |
| 2002/0013542 A1 | 1/2002 | Bonadio et al. |
| 2002/0016607 A1 | 2/2002 | Bonadio et al. |
| 2002/0026230 A1 | 2/2002 | Moll et al. |
| 2002/0038077 A1 | 3/2002 | de la Torre et al. |
| 2002/0072762 A1 | 6/2002 | Bonadio et al. |
| 2002/0111536 A1 | 8/2002 | Cuschieri et al. |
| 2002/0156432 A1 | 10/2002 | Racenet |
| 2002/0162559 A1 | 11/2002 | Crook |
| 2003/0004253 A1 | 1/2003 | Chen |
| 2003/0028179 A1 | 2/2003 | Piskun |
| 2003/0040711 A1 | 2/2003 | Racenet et al. |
| 2003/0078478 A1 | 4/2003 | Bonadio et al. |
| 2003/0139756 A1 | 7/2003 | Brustad |
| 2003/0167040 A1 | 9/2003 | Bacher et al. |
| 2003/0187376 A1 | 10/2003 | Rambo |
| 2003/0192553 A1 | 10/2003 | Rambo |
| 2003/0225392 A1 | 12/2003 | McMichael et al. |
| 2003/0236505 A1 | 12/2003 | Bonadio et al. |
| 2003/0236549 A1 | 12/2003 | Bonadio et al. |
| 2004/0015185 A1 | 1/2004 | Ewers et al. |
| 2004/0024363 A1 | 2/2004 | Goldberg |
| 2004/0049099 A1 | 3/2004 | Ewers et al. |
| 2004/0049100 A1 | 3/2004 | Butler |
| 2004/0054353 A1 | 3/2004 | Taylor |
| 2004/0063833 A1 | 4/2004 | Chen |
| 2004/0068232 A1 | 4/2004 | Hart et al. |
| 2004/0070187 A1 | 4/2004 | Chen |
| 2004/0072942 A1 | 4/2004 | Chen |
| 2004/0073090 A1 | 4/2004 | Butler |
| 2004/0092795 A1 | 5/2004 | Bonadio et al. |
| 2004/0092796 A1 | 5/2004 | Butler et al. |
| 2004/0093018 A1 | 5/2004 | Johnson |
| 2004/0097793 A1 | 5/2004 | Butler et al. |
| 2004/0106942 A1 | 6/2004 | Taylor et al. |
| 2004/0111061 A1 | 6/2004 | Curran |
| 2004/0127772 A1 | 7/2004 | Ewers et al. |
| 2004/0138529 A1 | 7/2004 | Wiltshire et al. |
| 2004/0143158 A1 | 7/2004 | Hart et al. |
| 2004/0154624 A1 | 8/2004 | Bonadio et al. |
| 2004/0167559 A1 | 8/2004 | Taylor et al. |
| 2004/0173218 A1 | 9/2004 | Yamada et al. |
| 2004/0215063 A1 | 10/2004 | Bonadio et al. |
| 2004/0230161 A1 | 11/2004 | Zeiner |
| 2004/0243144 A1 | 12/2004 | Bonadio et al. |
| 2004/0249248 A1 | 12/2004 | Bonadio et al. |
| 2004/0254426 A1 | 12/2004 | Wenchell |
| 2004/0260244 A1 | 12/2004 | Piechowicz et al. |
| 2004/0267096 A1 | 12/2004 | Caldwell et al. |
| 2005/0020884 A1 | 1/2005 | Hart et al. |
| 2005/0033246 A1 | 2/2005 | Ahlberg et al. |
| 2005/0059865 A1 | 3/2005 | Kahle et al. |
| 2005/0065475 A1 | 3/2005 | Hart et al. |
| 2005/0065543 A1 | 3/2005 | Kahle et al. |
| 2005/0090713 A1 | 4/2005 | Gonzales et al. |
| 2005/0090716 A1 | 4/2005 | Bonadio et al. |
| 2005/0090717 A1 | 4/2005 | Bonadio et al. |
| 2005/0096695 A1 | 5/2005 | Olich |
| 2005/0131349 A1 | 6/2005 | Albrecht et al. |
| 2005/0148823 A1 | 7/2005 | Vaugh et al. |
| 2005/0155611 A1 | 7/2005 | Vaugh et al. |
| 2005/0159647 A1 | 7/2005 | Hart et al. |
| 2005/0192483 A1 | 9/2005 | Bonadio et al. |
| 2005/0192598 A1 | 9/2005 | Johnson et al. |
| 2005/0197537 A1 | 9/2005 | Bonadio et al. |
| 2005/0203346 A1 | 9/2005 | Bonadio et al. |
| 2005/0209510 A1 | 9/2005 | Bonadio et al. |
| 2005/0222582 A1 | 10/2005 | Wenchell |
| 2005/0240082 A1 | 10/2005 | Bonadio et al. |
| 2005/0241647 A1 | 11/2005 | Nguyen |
| 2005/0251124 A1 | 11/2005 | Zvuloni et al. |
| 2005/0261720 A1 | 11/2005 | Caldwell et al. |
| 2005/0267419 A1 | 12/2005 | Smith |
| 2005/0277946 A1 | 12/2005 | Greenhalgh |
| 2005/0283050 A1 | 12/2005 | Gundlapalli et al. |
| 2005/0288558 A1 | 12/2005 | Ewers et al. |
| 2005/0288634 A1 | 12/2005 | O'Heeron et al. |
| 2006/0020164 A1 | 1/2006 | Butler et al. |
| 2006/0020241 A1 | 1/2006 | Piskun et al. |
| 2006/0030755 A1 | 2/2006 | Ewers et al. |
| 2006/0041270 A1 | 2/2006 | Lenker et al. |
| 2006/0047284 A1 | 3/2006 | Gresham |
| 2006/0047293 A1 | 3/2006 | Haberland et al. |
| 2006/0052669 A1 | 3/2006 | Hart |
| 2006/0084842 A1 | 4/2006 | Hart et al. |
| 2006/0106402 A1 | 5/2006 | McLucas |
| 2006/0129165 A1 | 6/2006 | Edoga et al. |
| 2006/0149137 A1 | 7/2006 | Pingleton et al. |
| 2006/0149306 A1 | 7/2006 | Hart et al. |
| 2006/0161049 A1 | 7/2006 | Beane et al. |
| 2006/0161050 A1 | 7/2006 | Butler et al. |
| 2006/0241651 A1 | 10/2006 | Wilk |
| 2006/0247498 A1 | 11/2006 | Bonadio et al. |
| 2006/0247499 A1 | 11/2006 | Butler et al. |
| 2006/0247500 A1 | 11/2006 | Voegele et al. |
| 2006/0247516 A1 | 11/2006 | Hess et al. |
| 2006/0247586 A1 | 11/2006 | Voegele et al. |
| 2006/0247673 A1 | 11/2006 | Voegele et al. |
| 2006/0247678 A1 | 11/2006 | Weisenburgh, II et al. |
| 2006/0258899 A1 | 11/2006 | Gill et al. |
| 2006/0264706 A1 | 11/2006 | Piskun |
| 2006/0270911 A1 | 11/2006 | Voegele et al. |
| 2007/0004968 A1 | 1/2007 | Bonadio et al. |
| 2007/0049966 A1 | 3/2007 | Bonadio et al. |
| 2007/0093695 A1 | 4/2007 | Bonadio et al. |
| 2007/0097793 A1 | 5/2007 | Butler et al. |
| 2007/0118175 A1 | 5/2007 | Butler et al. |
| 2007/0151566 A1 | 7/2007 | Kahle et al. |
| 2007/0156023 A1 | 7/2007 | Frasier et al. |
| 2007/0203398 A1 | 8/2007 | Bonadio et al. |
| 2007/0208312 A1 | 9/2007 | Norton et al. |
| 2007/0255219 A1 | 11/2007 | Vaugh et al. |
| 2007/0299387 A1 | 12/2007 | Williams et al. |
| 2008/0027476 A1 | 1/2008 | Piskun |
| 2008/0048011 A1 | 2/2008 | Weller |
| 2008/0097162 A1 | 4/2008 | Bonadio et al. |
| 2008/0097163 A1 | 4/2008 | Butler et al. |
| 2008/0200767 A1 | 8/2008 | Ewers et al. |
| 2008/0255519 A1 | 10/2008 | Piskun et al. |
| 2008/0281161 A1 | 11/2008 | Albrecht et al. |
| 2008/0281162 A1 | 11/2008 | Albrecht et al. |
| 2009/0012477 A1 | 1/2009 | Norton et al. |
| 2009/0036745 A1 | 2/2009 | Bonadio et al. |
| 2009/0069837 A1 | 3/2009 | Bonadio et al. |
| 2009/0093683 A1 | 4/2009 | Richard et al. |
| 2009/0093752 A1 | 4/2009 | Richard et al. |
| 2009/0131754 A1 | 5/2009 | Ewers et al. |
| 2009/0137879 A1 | 5/2009 | Ewers et al. |
| 2009/0149714 A1 | 6/2009 | Bonadio |
| 2009/0182279 A1 | 7/2009 | Wenchell et al. |
| 2009/0187079 A1 | 7/2009 | Albrecht et al. |
| 2009/0227843 A1 | 9/2009 | Smith et al. |
| 2009/0292176 A1 | 11/2009 | Bonadio et al. |
| 2009/0326330 A1 | 12/2009 | Bonadio et al. |
| 2010/0063362 A1 | 3/2010 | Bonadio et al. |
| 2010/0063364 A1 | 3/2010 | Bonadio et al. |
| 2010/0081880 A1 | 4/2010 | Widenhouse et al. |
| 2010/0081881 A1 | 4/2010 | Murray et al. |
| 2010/0081995 A1 | 4/2010 | Widenhouse et al. |
| 2010/0100043 A1 | 4/2010 | Racenet |
| 2010/0113882 A1 | 5/2010 | Widenhouse et al. |
| 2010/0217087 A1 | 8/2010 | Bonadio et al. |
| 2010/0228091 A1 | 9/2010 | Widenhouse et al. |
| 2010/0228092 A1 | 9/2010 | Ortiz et al. |
| 2010/0228094 A1 | 9/2010 | Ortiz et al. |
| 2010/0240960 A1 | 9/2010 | Richard |
| 2010/0249523 A1 | 9/2010 | Spiegel et al. |
| 2010/0249524 A1 | 9/2010 | Ransden et al. |
| 2010/0249525 A1 | 9/2010 | Shelton, IV et al. |
| 2010/0249694 A1 | 9/2010 | Choi et al. |
| 2010/0261972 A1 | 10/2010 | Widenhouse et al. |
| 2010/0261975 A1 | 10/2010 | Huey et al. |

| | | | |
|---|---|---|---|
| 2010/0286484 A1 | 11/2010 | Stellon et al. | |
| 2010/0298646 A1 | 11/2010 | Stellon et al. | |
| 2011/0021877 A1 | 1/2011 | Fortier et al. | |
| 2011/0028891 A1 | 2/2011 | Okoniewski | |
| 2011/0034935 A1 | 2/2011 | Kleyman | |
| 2011/0034946 A1 | 2/2011 | Kleyman | |
| 2011/0034947 A1 | 2/2011 | Kleyman | |
| 2011/0071462 A1 | 3/2011 | Ewers et al. | |
| 2011/0071463 A1 | 3/2011 | Ewers et al. | |

FOREIGN PATENT DOCUMENTS

| | | |
|---|---|---|
| DE | 33 36 279 C2 | 1/1986 |
| DE | 37 39 532 | 12/1988 |
| DE | 37 37 121 | 5/1989 |
| DE | 296 00 939 | 6/1996 |
| DE | 19828009 | 12/1999 |
| EP | 0113520 | 7/1984 |
| EP | 0142262 | 5/1985 |
| EP | 0 517 248 | 12/1992 |
| EP | 0537768 | 4/1993 |
| EP | 0 807 416 | 11/1997 |
| EP | 0 849 517 | 6/1998 |
| EP | 0950376 | 10/1999 |
| EP | 1118657 | 7/2001 |
| EP | 1 125 552 | 8/2001 |
| EP | 1312318 | 5/2003 |
| EP | 1 407 715 | 4/2004 |
| EP | 2044889 | 4/2009 |
| FR | 1456623 | 9/1966 |
| GB | 1151993 | 5/1969 |
| GB | 1355611 | 6/1974 |
| GB | 1372491 | 10/1974 |
| GB | 1379772 | 1/1975 |
| GB | 1400808 | 7/1975 |
| GB | 1407023 | 9/1975 |
| GB | 1482857 | 8/1977 |
| GB | 1496696 | 12/1977 |
| GB | 2071502 | 9/1981 |
| GB | 2255019 | 10/1992 |
| GB | 2275420 | 8/1994 |
| GB | 2298906 | 9/1996 |
| IE | 930649 | 9/1993 |
| IE | 930650 | 9/1993 |
| IE | S940150 | 2/1994 |
| IE | S940613 | 8/1994 |
| IE | S940960 | 12/1994 |
| IE | S950055 | 1/1995 |
| IE | S950266 | 4/1995 |
| IE | S940150 | 10/1995 |
| IE | S950055 | 7/1996 |
| IE | S71634 | 2/1997 |
| IE | S950266 | 2/1997 |
| IE | S75368 | 8/1997 |
| IE | S960196 | 8/1997 |
| IE | S970810 | 11/1997 |
| IE | 991010 | 7/2000 |
| IE | 990218 | 11/2000 |
| IE | 990219 | 11/2000 |
| IE | 990220 | 11/2000 |
| IE | 990660 | 2/2001 |
| IE | 990795 | 3/2001 |
| JP | 10-108868 | 4/1998 |
| JP | 11-290327 | 10/1999 |
| JP | 2001-61850 | 3/2001 |
| JP | 2002-28163 | 1/2002 |
| JP | 02003 235879 A | 8/2003 |
| JP | 2004-195037 | 7/2004 |
| SU | 1342485 | 1/1997 |
| WO | WO 86/06272 | 11/1986 |
| WO | WO 86/06316 | 11/1986 |
| WO | WO 92/11880 | 7/1992 |
| WO | WO 92/21292 | 12/1992 |
| WO | WO 93/05740 | 4/1993 |
| WO | WO 93/14801 | 8/1993 |
| WO | WO 94/04067 | 3/1994 |
| WO | WO 94/22357 | 10/1994 |
| WO | WO 95/05207 | 2/1995 |
| WO | WO 95/07056 | 3/1995 |
| WO | WO95/07056 | 3/1995 |
| WO | WO 95/22289 | 8/1995 |
| WO | WO95/22289 | 8/1995 |
| WO | WO 95/24864 | 9/1995 |
| WO | WO 95/27445 | 10/1995 |
| WO | WO 95/27468 | 10/1995 |
| WO | WO 96/36283 | 11/1996 |
| WO | WO 97/11642 | 4/1997 |
| WO | WO 97/32514 | 9/1997 |
| WO | WO 97/32515 | 9/1997 |
| WO | WO 97/42889 | 11/1997 |
| WO | WO 98/19853 | 5/1998 |
| WO | WO 98/35614 | 8/1998 |
| WO | WO 98/48724 | 11/1998 |
| WO | WO 99/03416 | 1/1999 |
| WO | WO 99/15068 | 4/1999 |
| WO | WO 99/16368 | 4/1999 |
| WO | WO 99/22804 | 5/1999 |
| WO | WO 99/25268 | 5/1999 |
| WO | WO 99/29250 | 6/1999 |
| WO | WO 00/32116 | 6/2000 |
| WO | WO 00/32119 | 6/2000 |
| WO | WO 00/32120 | 6/2000 |
| WO | WO 00/35356 | 6/2000 |
| WO | WO 00/321176 | 6/2000 |
| WO | WO 0035356 | 6/2000 |
| WO | WO 00/32120 | 8/2000 |
| WO | WO 00/54675 | 9/2000 |
| WO | WO 00/54676 | 9/2000 |
| WO | WO00/54676 | 9/2000 |
| WO | WO00/54677 | 9/2000 |
| WO | WO 00/54677 | 9/2000 |
| WO | WO0054675 | 9/2000 |
| WO | WO 01/08563 | 2/2001 |
| WO | WO 01/08581 | 2/2001 |
| WO | WO01/08581 | 2/2001 |
| WO | WO 01/26558 | 4/2001 |
| WO | WO 01/26559 | 4/2001 |
| WO | WO 01/45568 | 6/2001 |
| WO | WO 01/045568 | 6/2001 |
| WO | WO 01/49363 | 7/2001 |
| WO | WO 01/91652 | 12/2001 |
| WO | WO 02/07611 | 1/2002 |
| WO | WO 02/17800 | 3/2002 |
| WO | WO02/34108 | 5/2002 |
| WO | WO 02/34108 | 5/2002 |
| WO | WO 03/011153 | 2/2003 |
| WO | WO 03/011551 | 2/2003 |
| WO | WO 03/026512 | 4/2003 |
| WO | WO 03/028523 | 4/2003 |
| WO | WO 03/032819 | 4/2003 |
| WO | WO03/032819 | 4/2003 |
| WO | WO03/034908 | 5/2003 |
| WO | WO 03/034908 | 5/2003 |
| WO | WO 03/061480 | 7/2003 |
| WO | WO03/061480 | 7/2003 |
| WO | WO 03/077726 | 9/2003 |
| WO | WO 03/103548 | 12/2003 |
| WO | WO 2004/026153 | 4/2004 |
| WO | WO 2004/030547 | 4/2004 |
| WO | WO 2004/075730 | 9/2004 |
| WO | WO 2004/075730 A2 | 9/2004 |
| WO | WO 2004/075730 A3 | 9/2004 |
| WO | WO 2004/075741 | 9/2004 |
| WO | WO 2004/075741 A2 | 9/2004 |
| WO | WO 2004/075741 A3 | 9/2004 |
| WO | WO 2004/075930 | 9/2004 |
| WO | WO 2004/075930 A2 | 9/2004 |
| WO | WO 2004/075930 A3 | 9/2004 |
| WO | WO 2005/009257 | 2/2005 |
| WO | WO 2005/034766 | 4/2005 |
| WO | WO 2005/034766 A2 | 4/2005 |
| WO | WO 2005/089661 | 9/2005 |
| WO | WO 2006/040748 | 4/2006 |
| WO | WO 2006/059318 | 6/2006 |
| WO | WO 2006/100658 | 9/2006 |
| WO | WO 2008/015566 | 2/2008 |
| WO | WO 2008/093313 | 8/2008 |

| | | |
|---|---|---|
| WO | WO 2008/121294 | 10/2008 |
| WO | WO 2010/082722 | 7/2010 |
| WO | WO 2010/104259 | 9/2010 |

OTHER PUBLICATIONS

Horigane, et al., Technical Note: Development of a Duodoenal Cannula for Sheep, Journal of Animal Science, Apr. 1992, vol. 70, Issue 4, pp. 1216-1219.
Horigane, et al., Silicone Rumen Cannula with a Soft Cylindrical Part and a Hard Flange, Journal of Dairy Science, Nov., 1989, vol. 72, No. 11, pp. 3230-3232.
McSweeney, Cannullation of the Rumen in Cattle and Buffaloes, Australian Veterinary Journal, Aug., 1989, vol. 66, No. 8, pp. 266-268.
Yamazaki et al., Diurnal Changes in the Composition of Abomasal Digesta in Fasted and Fed Sheep, The Tohoku Journal of Argircultural Research, Mar. 1987, vol. 37, No. 3-4, pp. 49-58.
European Patent Office, Supplementary European Search Report for European Application No. EP 01 97 3379, dated Jul. 5, 2007, based on International Patent Application No. PCT/U.
Co-Pending U.S. Appl. No. 11/548,781, filed Oct. 12, 2006; Title: Wound Retractor With Gel Cap.
Co-Pending U.S. Appl. No. 11/548,955, filed Oct. 12, 2006; Title: Hand Access Laparoscopic Device.
Co-Pending U.S. Appl. No. 11/564,409, filed Nov. 29, 2006; Title: Surgical Instrument Access Device.
Co-Pending U.S. Appl. No. 10/381,220, filed Mar. 20, 2003; Title: Surgical Access Apparatus and Method.
Co-Pending U.S. Appl. No. 11/755,305, filed May 30, 2007; Title: Wound Retraction Apparatus and Method.
Co-Pending U.S. Appl. No. 10/927,551, filed Aug. 25, 2004; Title: Surgical Access System.
Co-Pending U.S. Appl. No. 11/244,647, filed Oct. 5, 2005; Title: Surgical Access Apparatus and Method.
Co-Pending U.S. Appl. No. 11/245,709, filed Oct. 7, 2005; Title: Surgical Access System.
Co-Pending U.S. Appl. No. 11/330,661, filed Jan. 12, 2006; Title: Sealed Surgical Access Device.
Co-Pending U.S. Appl. No. 11/548,746, filed Oct. 12, 2006; Title Method of Making a Hand Access Laparoscopic Device.
Co-Pending U.S. Appl. No. 11/548,758, filed Oct. 12, 2006; Title: Split Hoop Wound Retractor With Gel Pad.
Co-Pending U.S. Appl. No. 11/548,765, filed Oct. 12, 2006; Title: Split Hoop Wound Retractor.
Co-Pending U.S. Appl. No. 11/548,767, filed Oct. 12, 2006; Title: Circular Surgical Retractor.
US Patent Office, International Search Report and The Written Opinion of the International Searching Authority for PCT Application No. PCT/US2004/05484.
European Patent Office, International Search Report and The Written Opinion of the International Searching Authority for PCT Application No. PCT/US2006/039799 mailed Mar. 27, 2007.
European Patent Office, International Search Report and The Written Opinion of the International Searching Authority for PCT Application No. PCT/US2006/039800 mailed Apr. 16, 2007.
European Patent Office, International Search Report and Written Opinion of the International Searching Authority for International Application No. PCT/US2006/039883, mailed Jan. 31, 2007.
European Patent Office, International Search Report and Written Opinion of the International Searching Authority for International Application No. PCT/US2006/039905, mailed Jan. 17, 2007.
European Patent Office, International Search Report and The Written Opinion of the International Searching Authority for International Application No. PCT/US2006/040073, Jan. 26, 2007.
International Search Report and Written Opinion of the International Searching Authority for PCT application No. PCT/US01/29682.
Technical Note: Development of a Duodenal Cannula for Sheep, Faculty of Agriculture and Schol of Medicine Tohoku University, Sendai 981, Japan.
The International Bureau of WIPO, International Preliminary Report on Patentability, dated Aug. 29, 2006, for international application No. PCT/US20041028250.
The International Bureau of WIPO, International Preliminary Report on Patentability dated Apr. 16, 2008 for PCT Application No. PCT/US2006/039799.
Co-Pending U.S. Appl. No. 12/108,400, filed Apr. 23, 2008; Title Wound Retraction Apparatus and Method.
European Patent Office, Supplementary European Search Report for European Patent Application No. EP 03 75 7319, based on International Application No. PCT/US03/17389, dated Jan. 19, 2009, entitled "Wound Retractor".
European Patent Office, European Search Report for European Patent Application No. EP 11 16 2161 dated Jun. 20, 2011.
US 5,334,646, Chen (withdrawn).
U.S. Appl. No. 10/381,220, filed Mar. 20, 2003; Title: Surgical Access Apparatus and Method, now USPN 7,473,221 issued Jan. 6, 2009.
U.S. Appl. No. 10/436,522, filed May 13, 2003; Title: Laparoscopic Illumination Apparatus and Method, now USPN 6,939,296 issued Sep. 6, 2005.
U.S. Appl. No. 10/399,209, filed Aug. 22, 2003; Title: Wound Retraction Apparatus and Method, now USPN 6,958,037 issued Oct. 25, 2005.
U.S. Appl. No. 11/218,412, filed Sep. 1, 2005; Title: Wound Retraction Apparatus and Method, now USPN 7,238,154 issued Jul. 3, 2007.
U.S. Appl. No. 10/399,057, filed Apr. 11, 2003; Title: Sealed Surgical Access Device, now USPN 7,052,454 issued May 30, 2006.
U.S. Appl. No. 10/666,579, filed Sep. 17, 2003; Title: Surgical Instrument Access Device, now USPN 7,163,510 issued Jan. 16, 2007.
U.S. Appl. No. 10/052,297, filed Jan. 18, 2002; Title: Hand Access Port Device, now USPN 6,908,430 issued Jun. 21, 2005.
U.S. Appl. No. 08/015,765, filed Feb. 10, 1993; Title: Gas-Tight Seal Accomodating Surgical Instruments With a Wide Range of Diameters, now USPN 5,407,433 issued Apr. 18, 1995.
U.S. Appl. No. 08/040,373, filed Mar. 30, 1993; Title: Gas-Tight Seal Accomodating Surgical Instruments With a Wide Range of Diameters, now USPN 5,411,483 issued May 2, 1995.
U.S. Appl. No. 10/902,756, filed Jul. 29, 2004; Title: Hand Access Port Device, now abandoned.
U.S. Appl. No. 10/802,125, filed Mar. 15, 2004; Title: Surgical Guide Valve, now abandoned.
U.S. Appl. No. 10/516,198, filed Nov. 30, 2004; Title: Wound Retractor, now USPN 7,650,887 issued Jan. 26, 2010.
U.S. Appl. No. 10/927,551, filed Aug. 25, 2004; Title: Surgical Access System, now abandoned.
U.S. Appl. No. 11/244,647, filed Oct. 5, 2005; Title: Surgical Access Apparatus and Method, now USPN 7,481,765 issued Jan. 27, 2009.
U.S. Appl. No. 11/548,746, filed Oct. 12, 2006; Title: Method of Making a Hand Access Laparoscopic Device, now USPN 7,749,415 issued Jul. 6, 2010.
U.S. Appl. No. 11/548,765, filed Oct. 12, 2006; Title: Split Hoop Wound Retractor, now USPN 7,815,567 issued Oct. 26, 2010.
U.S. Appl. No. 11/548,767, filed Oct. 12, 2006; Title: Circular Surgical Retractor now USPN 7,704,207 issued Apr. 27, 2010.
U.S. Appl. No. 11/548,781, filed Oct. 12, 2006; Title: Wound Retractor With Gel Cap, now USPN 7,727,146 issued Jun. 1, 2010.
U.S. Appl. No. 11/548,955, filed Oct. 12, 2006; Title: Hand Access Laparoscopic Device, now USPN 7,736,306 issued Jun. 15, 2010.
U.S. Appl. No. 11/755,305, filed May 30, 2007; Title: Wound Retraction Apparatus and Method, now USPN 7,377,898 issued May 27, 2008.
U.S. Appl. No. 11/548,758, filed Oct. 12, 2007; Title: Split Hoop Wound Retractor With Gel Pad, now USPN 7,909,760 issued Mar. 22, 2011.
U.S. Appl. No. 12/693,242, filed Jan. 1, 2010; Title: Wound Retractor, now USPN 7,913,697 issued Mar. 29, 2011.
U.S. Appl. No. 12/768,328, filed Apr. 27, 2010; Title: Circular Surgical Retractor, now USPN 7,892,172 issued Feb. 22, 2011.
U.S. Appl. No. 12/791,666, filed Jun. 1, 2010; Title: Wound Retractor With Gel Cap, now USPN 7,883,461 issued Feb. 8, 2011.
U.S. Appl. No. 12/815,986, filed Jun. 15, 2010; Title: Hand Access Laparoscopic Device, now USPN 7,878,974 issued Feb. 1, 2011.
U.S. Appl. No. 10/695,295, filed Oct. 28, 2003; Title: Surgical Gel Seal.

U.S. Appl. No. 11/132,741, filed May 18, 2005; Title: Gas-Tight Seal Accomodating Surgical Instruments With a Wide Range of Diameters.
U.S. Appl. No. 11/245,709, filed Oct. 7, 2005; Title: Surgical Access System.
U.S. Appl. No. 11/330,661, filed Jan. 12, 2006; Title: Sealed Surgical Access Device.
U.S. Appl. No. 11/564,409, filed Nov. 29, 2006; Title: Surgical Instrument Access Device.
U.S. Appl. No. 12/108,400, filed Apr. 23, 2008; Title: Wound Retraction Apparatus and Method.
U.S. Appl. No. 12/119,371, filed May 12, 2008; Title: Surgical Retractor With Gel Pad.
U.S. Appl. No. 12/119,414, filed May 12, 2008; Title: Surgical Retractor.
U.S. Appl. No. 12/358,080, filed Jan. 22, 2009; Title: Surgical Instrument Access Device.
U.S. Appl. No. 12/360,634, filed Jan. 27, 2009; Title: Surgical Access Apparatus and Method.
U.S. Appl. No. 12/360,710, filed Jan. 27, 2009; Title: Surgical Access Apparatus and Method.
U.S. Appl. No. 12/578,422, filed Oct. 13, 2009; Title: Single Port Access System.
U.S. Appl. No. 12/905,932, filed Oct. 15, 2010; Title: Split Hoop Wound Retractor.
U.S. Appl. No. 12/960,449, filed Dec. 3, 2010; Title: Surgical Access Apparatus and Method.
U.S. Appl. No. 12/960,458, filed Dec. 3, 2010; Title: Surgical Access Apparatus and Method.
U.S. Appl. No. 13/006,727, filed Jan. 14, 2011.
U.S. Appl. No. 13/008,728, filed Jan. 18, 2011.
U.S. Appl. No. 13/023,334, filed Feb. 8, 2011.
U.S. Appl. No. 13/031,892, filed Feb. 22, 2011.
U.S. Appl. No. 13/050,042, filed Mar. 17, 2011.
U.S. Appl. No. 10/446,365, filed May 28, 2003; Title: Screw-Type Seal With Inflatable Membrane.
U.S. Appl. No. 12/004,439, filed Dec. 20, 2007; Title: Skin Seal.
U.S. Appl. No. 12/004,441, filed Dec. 20, 2007; Title: Screw-Type Skin Seal With Inflatable Membrane.
U.S. Appl. No. 12/607,667, filed Oct. 28, 2009; Title: Screw-Type Skin Seal With Inflatable Membrane.
U.S. Appl. No. 10/965,217, filed Oct. 15, 2004; Title: Surgical Sealing Device.
U.S. Appl. No. 10/981,730, filed Nov. 5, 2004; Title: Surgical Sealing Device.
U.S. Appl. No. 11/246,909, filed Oct. 11, 2005; Title: Instrument Access Device.
U.S. Appl. No. 11/291,089, filed Dec. 1, 2005; Title: A Surgical Sealing Device.
U.S. Appl. No. 11/486,383, filed Jul. 14, 2006; Title: Wound Retractor.
U.S. Appl. No. 11/785,752, filed Apr. 19, 2007; Title: Instrument Access Device.
U.S. Appl. No. 12/244,024, filed Oct. 2, 2008; Title: Seal Anchor for use in Surgical Procedures.
U.S. Appl. No. 12/578,832, filed Oct. 14, 2009; Title: Flexible Access Device for Use in Surgical Procedure.
U.S. Appl. No. 12/706,043, filed Feb. 16, 2010; Title: Flexible Port Seal.
U.S. Appl. No. 12/719,341, filed Mar. 8, 2010; Title: Foam Port and Introducer Assembly.
U.S. Appl. No. 10/895,546, filed Jul. 21, 2004; Title: Laparoscopic Instrument and Cannula Assembly and Related Surgical Method.
U.S. Appl. No. 10/913,565, filed Aug. 5, 2004; Title: Surgical Device With Tack-Free Gel and Method of Manufacture.
Dexterity Protractor Instruction Manual by Dexterity Surgical, Inc.
European Patent Office, European Search Report for European Application No. EP 10 18 4681, dated Nov. 22, 2010, entitled "Wound Retraction Apparatus and Method".
European Patent Office, European Search Report for European Application No. EP 10 18 4608, dated Nov. 22, 2010, entitled "Wound Retraction Apparatus and Method".
European Patent Office, European Search Report for European Application No. EP 10 18 4648, dated Nov. 22, 2010, entitled "Wound Retraction Apparatus and Method".
European Patent Office, European Search Report for European Application No. EP 10 18 4731, dated Nov. 22, 2010, entitled "Wound Retraction Apparatus and Method".
European Patent Office, European Search Report for European Application No. EP 10 18 4661, dated Nov. 22, 2010, entitled "Wound Retraction Apparatus and Method".
European Patent Office, European Search Report for European Application No. EP 10 18 4677, dated Nov. 22, 2010, entitled "Wound Retraction Apparatus and Method".
European Patent Office, European Search Report for European Application No. EP 10 18 9325, dated Dec. 14, 2010, entitled "Split Hoop Wound Retractor".
European Patent Office, European Search Report for European Application No. EP 10 18 9327, dated Dec. 14, 2010, entitled "Split Hoop Wound Retractor".
European Patent Office, European Search Report for European Application No. EP 10 18 9328, dated Dec. 15, 2010, entitled "Split Hoop Wound Retractor".
European Patent Office, European Search Report for European Application No. EP 04 00 2888, dated Sep. 10, 2004, entitled "Hand Access Port Device".
European Patent Office, European Search Report for European Application No. EP 04 00 2889, dated Sep. 13, 2004, entitled "Hand Access Port Device".
European Patent Office, International Search Report and the Written Opinion of the International Searching Authority for International Application No. PCT/US2006/040154, mailed Jan. 30, 2007.
European Patent Office, International Search Report and the Written Opinion of the International Searching Authority for International Application No. PCT/US2006/040073, mailed Jan. 26, 2007.
European Patent Office, International Search Report and the Written Opinion of the International Searching Authority for International Application No. PCT/US2006/039905, mailed Jan. 17, 2007.
European Patent Office, International Search Report and the Written Opinion of the International Searching Authority for International Application No. PCT/US2006/039883, mailed Jan. 31, 2007.
European Patent Office, International Search Report and the Written Opinion of the International Searching Authority for International Application No. PCT/US2006/039800, mailed Apr. 16, 2007.
European Patent Office, International Search Report and the Written Opinion of the International Searching Authority for International Application No. PCT/US2006/039799, mailed Mar. 27, 2007.
European Search Report for corresponding EP 08253236 date of mailing is Feb. 10, 2009 (6 pages).
Horigame, et al., Silicone Rumen Cannula with a Soft Cylindrical Part and a Hard Flange, Journal of Dairy Science, Nov. 1989, vol. 72, No. 11, pp. 3230-3232.
Horigame, et al., Technical Note: Development of Duodoenal Cannula for Sheep, Journal of Animal Science, Apr. 1992, vol. 70, Issue 4, pp. 1216-1219.
International Searching Authority/US, International Search Report and the Written Opinion of the International Searching Authority for International Application No. PCT/US04/05484.
International Searching Authority/US, International Search Report and the Written Opinion of the International Searching Authority for International Application No. PCT/US01/29682.
McSweeney, Cannulation of the Rumen in Cattle and Buffaloes, Australian Veterinary Journal, Aug. 1989, vol. 66, No. 8, pp. 266-268.
Neil Sheehan, Supplemental Expert Report of Neil Sheehan, Re: U.S. Patent No. 5,741,298, United States District Court for the Central District of California, Civil Action No. SACV 03-1322 JVS, Aug. 9, 2005.
Office Action in co-pending U.S. Appl. No. 12/360,634, dated Jan. 24, 2011 in 12 pages.
Office Action in co-pending U.S. Appl. No. 12/360,710, dated Jan. 24, 2011 in 12 pages.
Technical Note: Development of Duodenal Cannula for Sheep, Faculty of Agriculture and School of Medicine Tohokju University, Sendai 981, Japan.

The International Bureau of WIPO, International Preliminary Report on Patentability, dated Aug. 29, 2006, for International Application No. PCT/US2004/028250.

The International Bureau of WIPO, International Preliminary Report on Patentability, dated Apr. 16, 2008, for International Application No. PCT/US2006/039799.

The International Bureau of WIPO, International Preliminary Report on Patentability for International Application No. PCT/US2006/039800 dated Apr. 16, 2008.

Yamazaki, et al., Diurnal Changes in the Composition of Abomasal Digesta in Fasted and Fed Sheep, The Tohoki Journal of Agricultural Research, Mar. 1987, vol. 37, No. 3-4, pp. 49-58.

Kagaya, Laparascopic cholecystecomy via two ports, using the "Twin-Port" system, J. Hepatobiliary Pancreat Surg (2001) 8:76-80.

International Search Report and Written Opinion in PCT/IE2005/000113 mailed on Feb. 22, 2006.

International Search Report and Written Opinion in PCT/IE2007/000050 mailed on Aug. 13, 2007.

Declaration of John R. Brustad dated Dec. 10, 2009, submitted in U.S. Appl. No. 11/548,955, including Appendices A-D regarding product sales brochures and production drawings from 2001 and 2005.

The International Searching Authority, The International Search Report and Written Opinion of the International Searching Authority for International Application No. PCT/US08/63445, mailed Sep. 29, 2008.

The International Searching Authority, The International Search Report and Written Opinion of the International Searching Authority for International Application No. PCT/US08/063463 mailed Sep. 10, 2008.

The International Bureau of WIPO, International Preliminary Report on Patentability for International Application No. PCT/US2008/063463, dated Nov. 17, 2009, entitled "Surgical Retractor".

The International Bureau of WIPO, International Preliminary Report on Patentability for International Application No. PCT/US08/63445, issued Nov. 17, 2009, entitled "Surgical Retractor with Gel Pad".

International Searching Authority-US, International Search Report and Written Opinion of the International Searching Authority for International Application No. PCT/US04/25511, mailed Nov. 7, 2007.

International Bureau of WIPO, International Report on Patentability for International Application No. PCT/US04/25511, mailed Dec. 6, 2007.

European Patent Office, European Search Report for European Patent Application No. EP 11 16 2165 dated May 19, 2011.

European Patent Office, European Search Report for European Patent Application No. EP 11 16 2164 dated Jun. 6, 2011.

European Patent Office, European Search Report for European Patent Application No. EP 11 16 2162 dated May 18, 2011.

European Patent Office, European Search Report for European Patent Application No. EP 11 16 2157 dated Jun. 6, 2011.

Harold W. Harrower, M.D. Isolation of Incisions into Body Cavities, The American Journal of Surgery, p. 824-826.

European Patent Office, European Search Report for European Patent No. 11172709.5, dated Aug. 16, 2011.

European Patent Office, European Search Report for European Patent No. 11172706.1, dated Aug. 16, 2011.

* cited by examiner

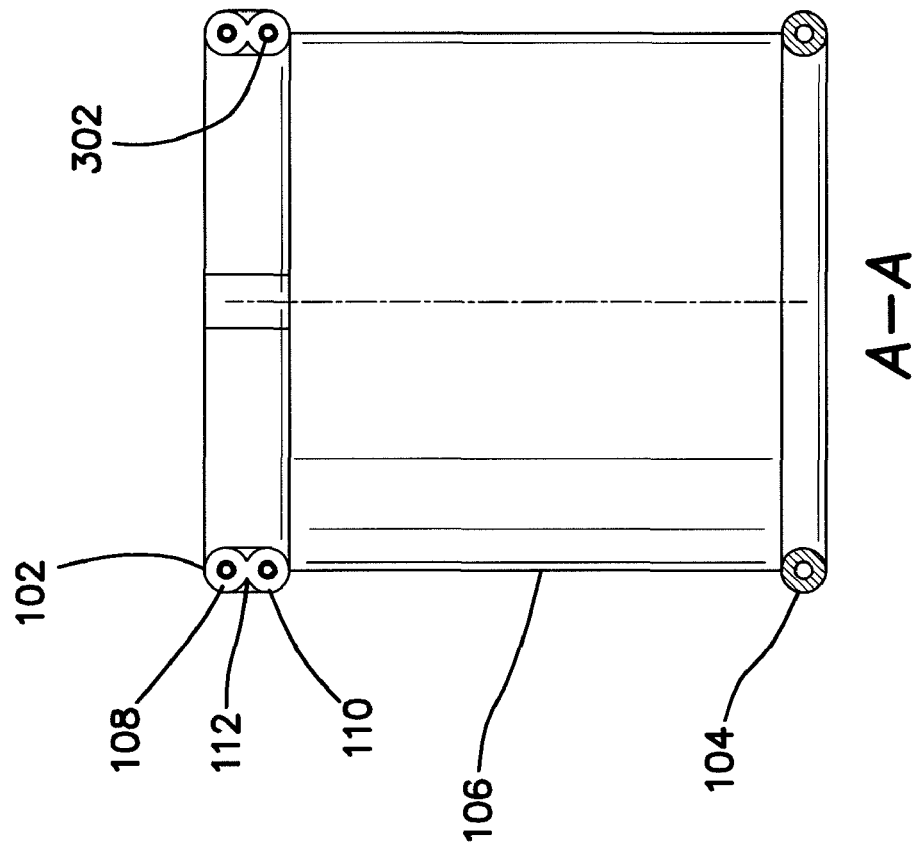
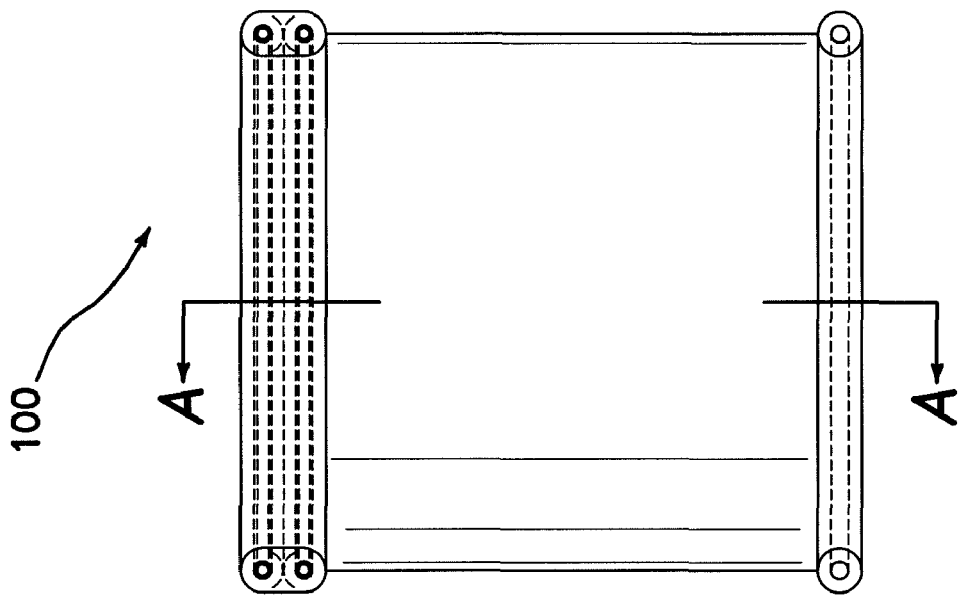
FIG. 3

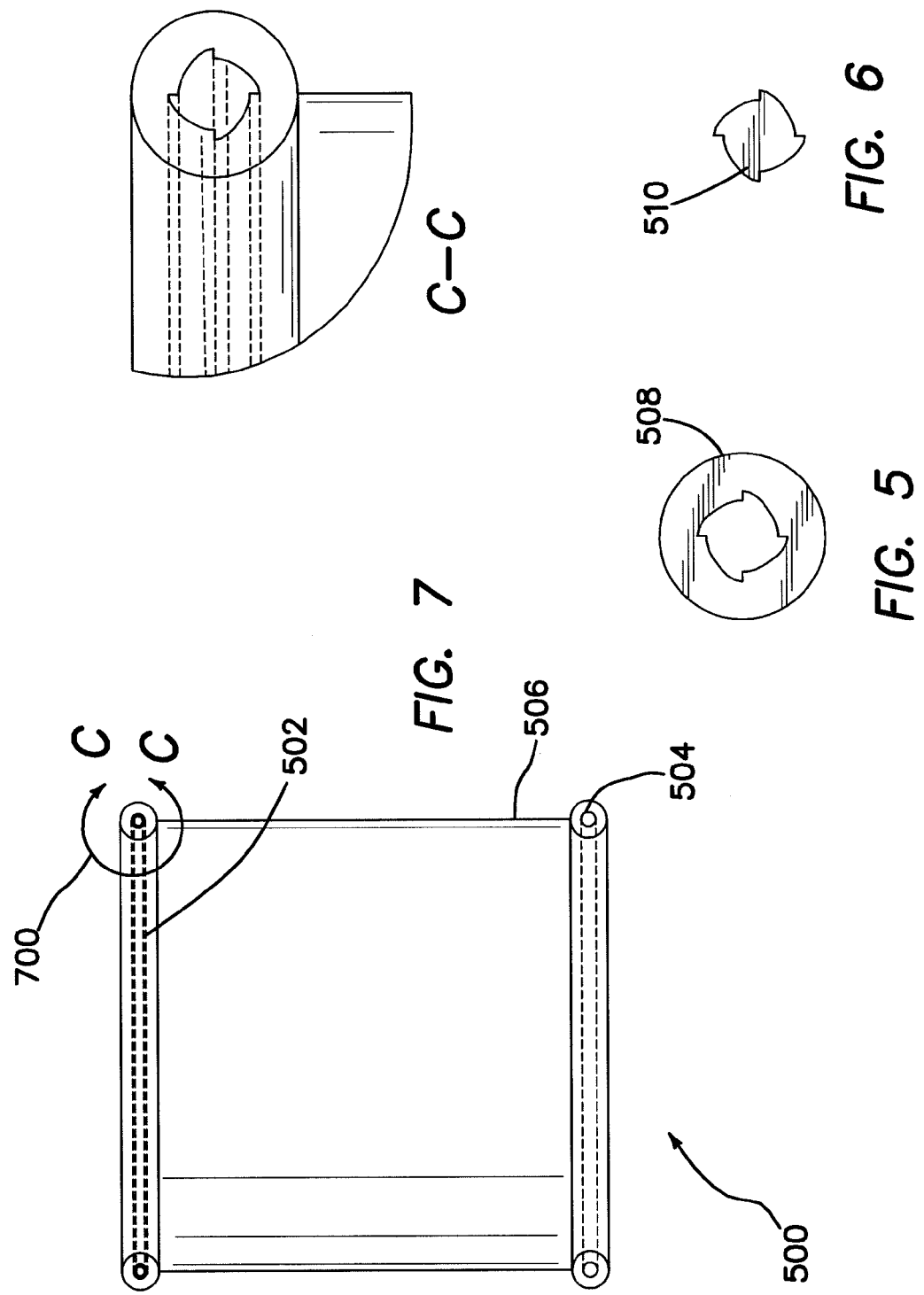

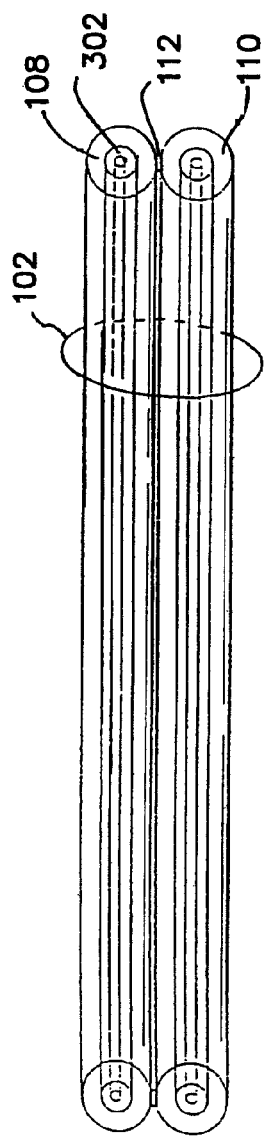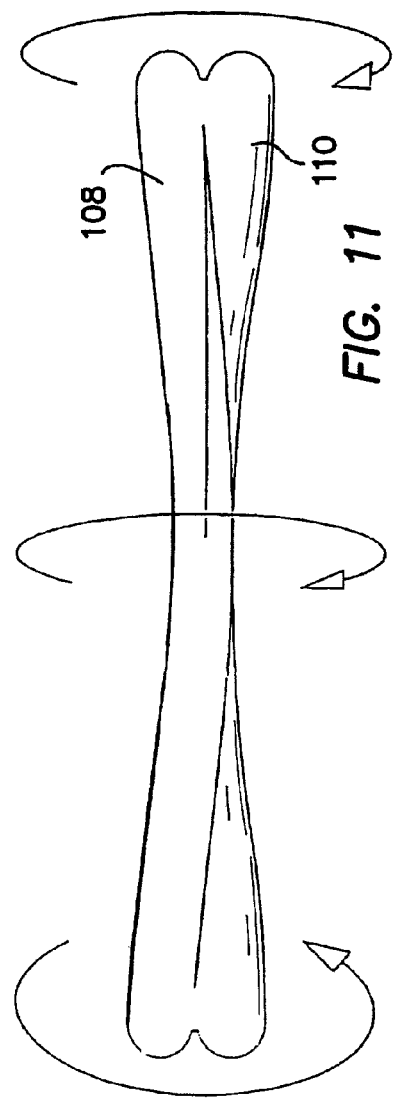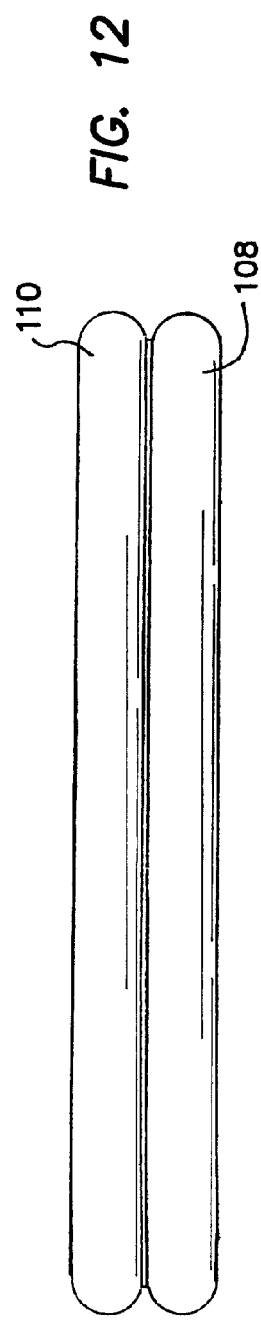

510

D-D

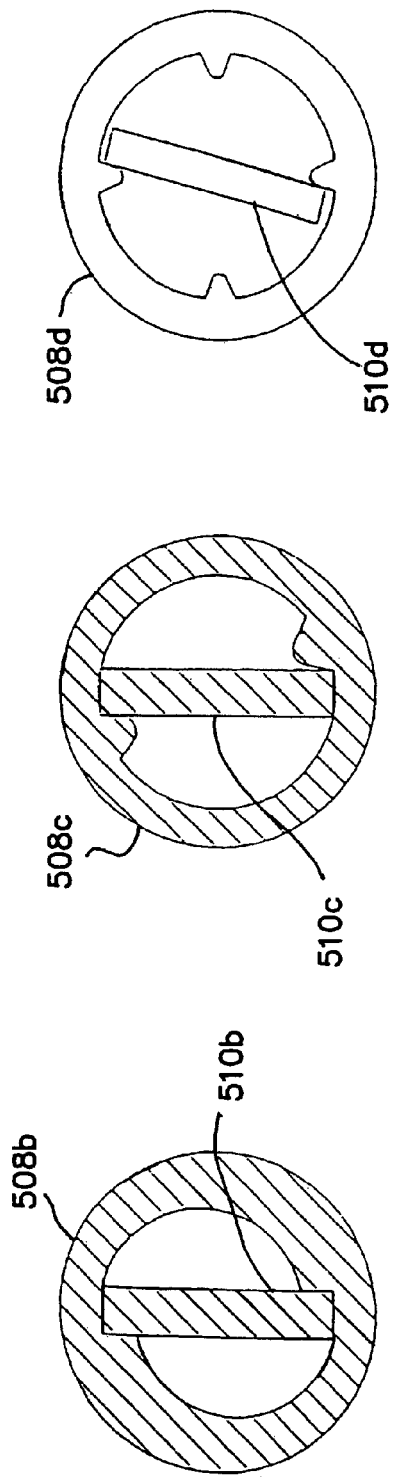
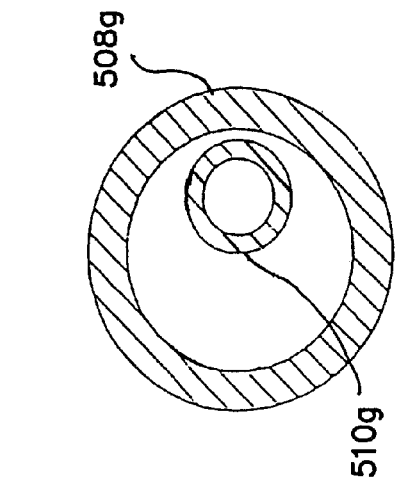
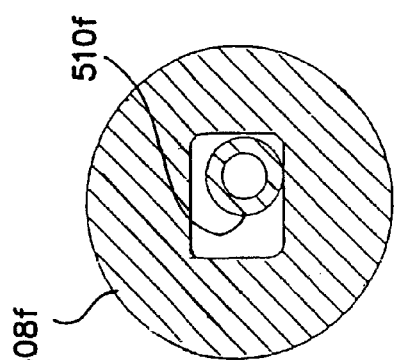
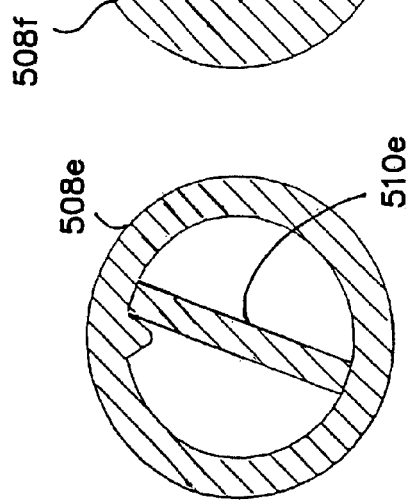
FIG. 18d
FIG. 18g
FIG. 18c
FIG. 18f
FIG. 18b
FIG. 18e

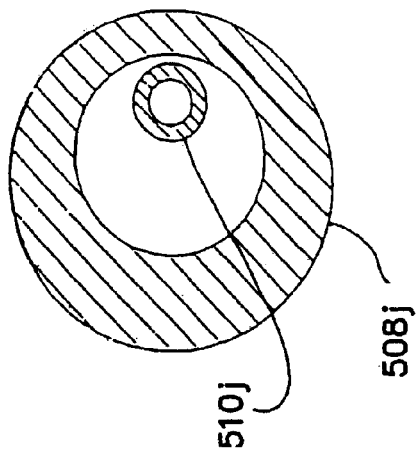
FIG. 18j
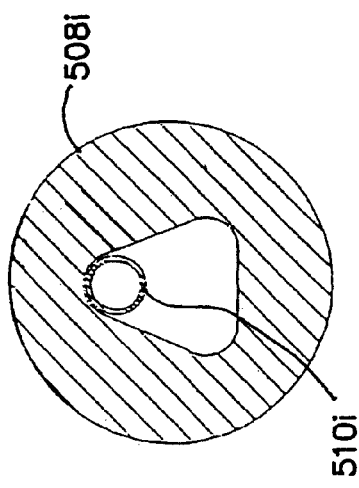
FIG. 18i
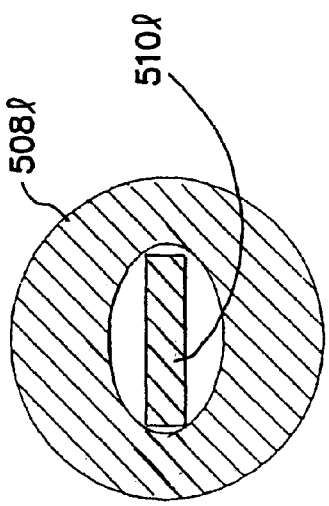
FIG. 18ℓ
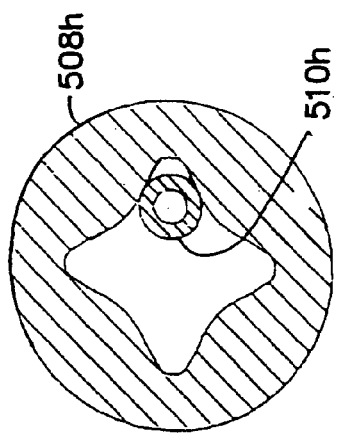
FIG. 18h
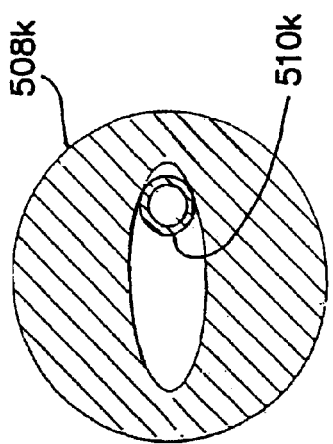
FIG. 18k

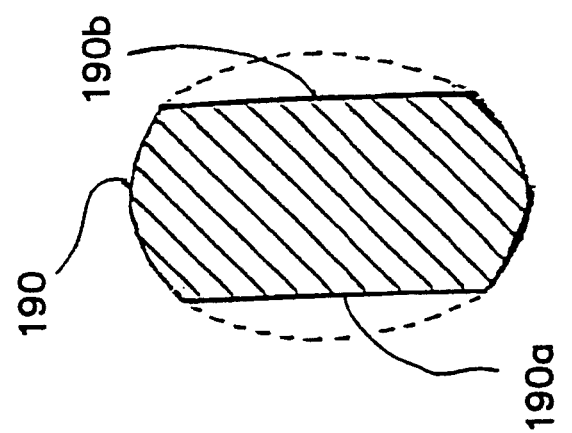
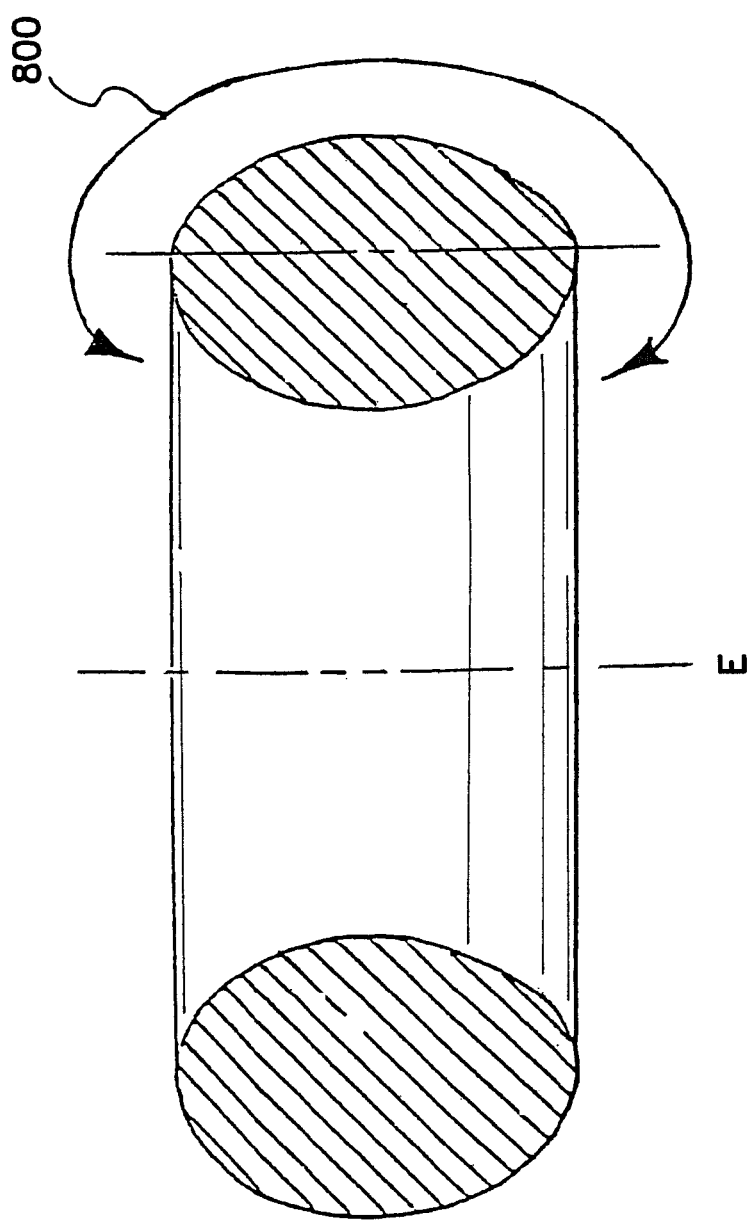
FIG. 19b
FIG. 19a

WOUND RETRACTOR

CROSS-REFERENCE TO RELATED APPLICATION

This application is a continuation of U.S. application Ser. No. 12/693,242, filed Jan. 25, 2010, now U.S. Pat. No. 7,913,697, issued Mar. 29, 2011, which is a continuation of U.S. application Ser. No. 10/516,198 now U.S. Pat. No. 7,650,887, which entered the National Phase under 35 U.S.C. §371 on Nov. 30, 2004 from International Application No. PCT/US2003/017389, filed Jun. 3, 2003, which was published in English on Dec. 18, 2003 as WO 03/103548 A1, now U.S. Pat. No. 7,650,887, issued Jan. 26, 2010, which claims the benefit of U.S. application Ser. No. 60/386,159, filed on Jun. 5, 2002, and U.S. application Ser. No. 60/415,351, filed on Oct. 2, 2002, the disclosures all of which are fully incorporated herein by reference.

BACKGROUND

1. Technical Field

This invention generally relates to medical devices and, more specifically, to an improved wound retractor providing ease of incremental retraction and alignment to fit a wide range of incision sizes, including audible and tactile feedback to the user.

2. Description of the Related Art

Surgery typically involves making an incision large enough to accommodate a surgeon's hand and/or multiple instruments. The incision must be kept clean since it is susceptible to infection if touched by diseased body parts and/or contaminated instruments. As such, wound protectors are available to insure that exposed sides of an incision are covered and protected from contaminants. A common deficiency of wound protectors is their lack of ease of retraction adjustability and stability. U.S. Pat. Nos. 5,524,644 and 6,382,211, both to Crook, attempt to address this deficiency with a wound protector including an outer ring having an oblate cross-section and opposed flat surfaces that allegedly provide retraction adjustability and stability. The oblate design of the outer ring of Crook, however, provides only limited incremental retraction and can be difficult to twist or turn. In addition, the Crook design does not provide for an audible feedback to the user. Accordingly, there is a need in the art for an improved wound retractor that can be easily retracted to fit a wide range of incision sizes. The improved wound retractor preferably provides audible and/or tactile feedback to the user during retraction.

SUMMARY OF THE INVENTION

An incrementally adjustable wound retractor for sealing edges of a surgical incision and forming an opening in a patient's body cavity, the wound retractor comprising an inner ring, an outer ring and a flexible sleeve connecting the inner ring and the outer ring. The wound retractor provides a path for a surgeon to insert his hand and/or instruments through the opening formed by the wound retractor. The wound retractor is incrementally adjustable to fit a wide range of incision sizes. The wound retractor is installed or placed in a body cavity such that the inner and outer rings expand around inner and outer edges of the incision. Any portion of the flexible sleeve extending outside the incision can be easily rolled onto the outer ring to tightly seal the sides of the wound. The outer ring is preferably shaped to provide audible and/or tactile feedback to the user. In particular, the outer ring includes surfaces that are easy to grip and turn to allow the user to manually turn the outer ring and roll up the flexible sleeve with ease. The outer ring may be solid or include a lumen with a rod placed therein to provide audible signal to the user as the outer ring is turned.

These and other features and advantages of the invention will become more apparent with a discussion of preferred embodiments in reference to the associated drawings.

BRIEF DESCRIPTION OF THE DRAWINGS

FIG. 3 is a longitudinal cross-section view of the wound retractor of FIG. 1 taken along line A-A;

FIG. 5 is a cross-section view of a hollow tube of an outer ring of a wound retractor in accordance with a second embodiment of the invention;

FIG. 6 is a cross-section view of an inner rod of the outer ring of the wound retractor in accordance with the second embodiment of the invention;

FIG. 7 illustrates a cutaway side view of an incrementally adjustable wound retractor in accordance with the second embodiment of the invention;

FIG. 10 illustrates a longitudinal cross-section view of an outer ring including a wire in accordance with a third embodiment of the invention;

FIGS. 11 and 12 illustrate the rolling of the outer ring to fit a desired incision size in accordance with the third embodiment of the invention;

FIGS. 18A-18L illustrate cross-section views of additional embodiments of the hollow tube and inner rod of the outer ring of the invention;

FIGS. 19A-19G illustrate cross-section views of additional embodiments of the outer ring of the invention having generally prolate cross-sections;

DETAILED DESCRIPTION OF CERTAIN EMBODIMENTS

Figure 1:
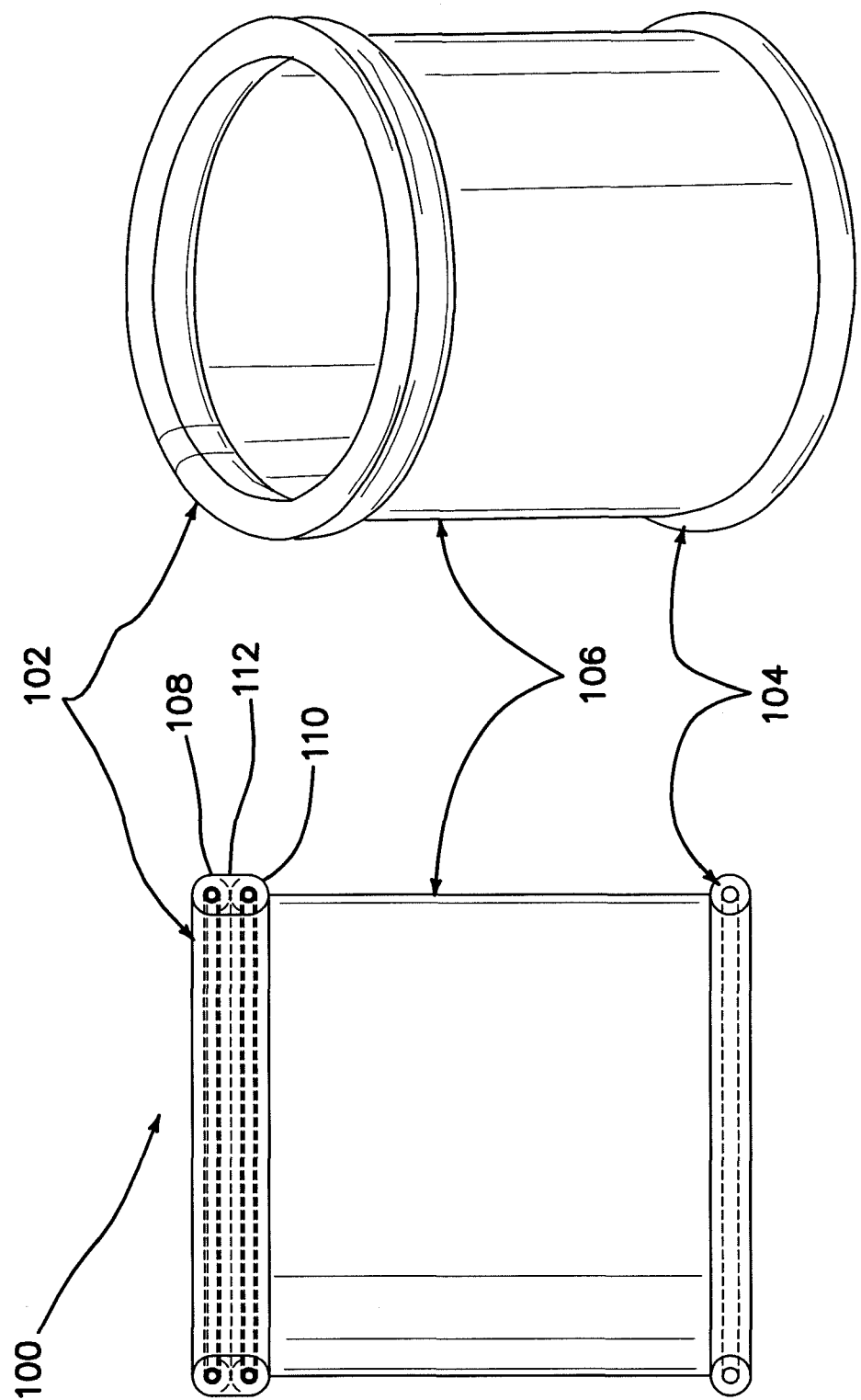
FIG. 1 illustrates a cutaway side view and an isometric view of an incrementally adjustable wound retractor in accordance with an embodiment of the invention.

FIG. 1 illustrates a wound retractor 100 in accordance with a first embodiment of the invention. The wound retractor 100 comprises a double-tube outer ring 102, an inner ring 104, and a distensible sleeve 106 connecting the outer ring 102 and the inner ring 104. The sleeve 106 may be attached to the outer ring 102 and the inner ring 104 by heat seal or adhesive. The outer ring 102 and the inner ring 104 are preferably made of a material of sufficient hardness to retain their shape after twisting and rolling of the rings. That is, the material must be compliant enough to allow the outer ring 102 to be turned around its annular axis as further described below and illustrated in FIGS. 2A-2D. The shape of the outer ring 102 affects both its ability to grip and to provide stability during and after adjustment. The sleeve 106 is preferably made of a material that is flexible and impermeable to fluids and bacteria. The double-tube outer ring 102 preferably comprises a first circular tube 108 and a second circular tube 110 joined together by a small web 112. Each of the circular tubes 108 and 110 may be solid or include a lumen.

FIGS. 2A-2D illustrate the retraction and adjustment of the outer ring 102 to fit an incision. In accordance with the invention, the wound retractor 100 is axially adjustable in increments. In particular, the upper end of the sleeve 106 can be wrapped around the outer ring 102 so as to tightly seal the sides or edges of the incision. The unique shape of the outer ring 102 provides for an easy snap action when rolled about itself. The outer ring 102 also provides for incremental shortening of the sleeve 106 and for stability after installation. FIG. 3 illustrates a longitudinal cross-section view of the wound retractor 100 taken along line A-A.

Figure 2A:
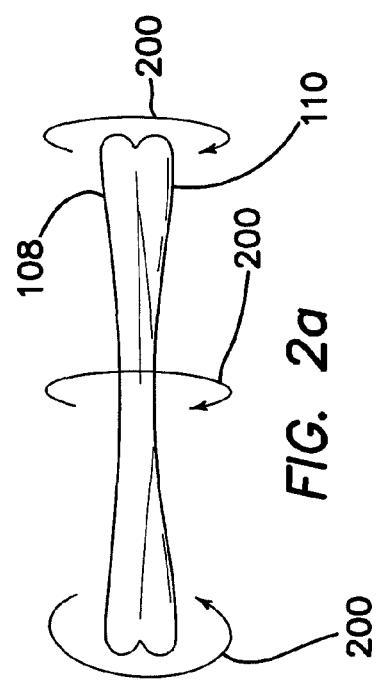
FIGS. 2A-2D illustrate the retraction of the outer ring of the wound retractor of FIG. 1 to fit a desired incision.
Figure 2B:
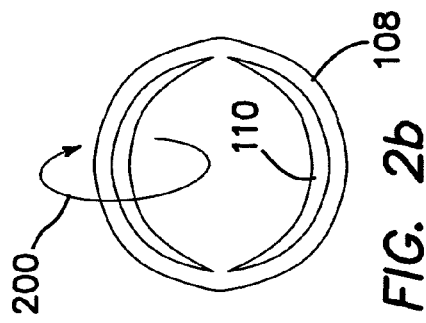
Figure 2C:
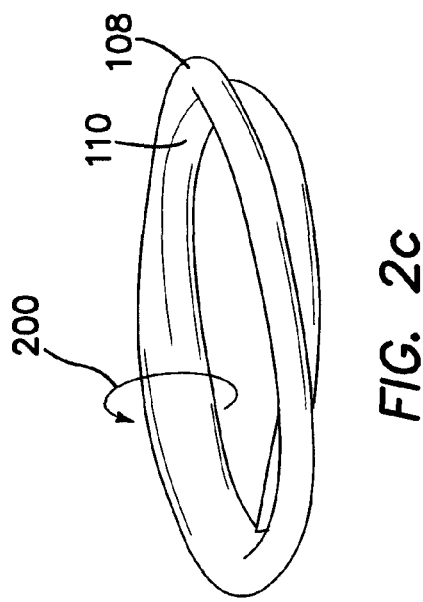
Figure 4:
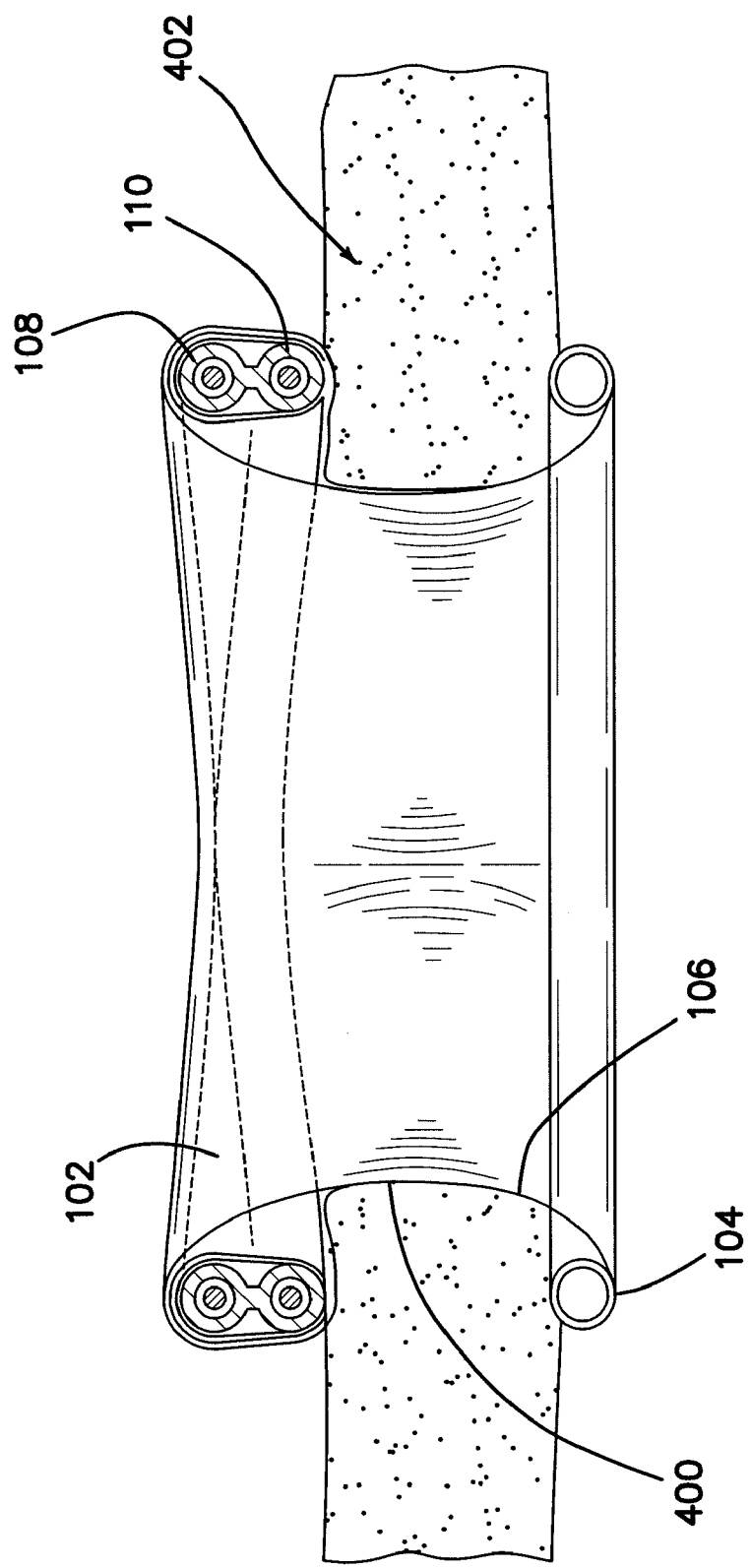
FIG. 4 illustrates the wound retractor of FIG. 1 installed in an incision.

FIG. 4 illustrates a process of installing the wound retractor 100 in a wound opening 400. An incision in the shape of a slit is first made in a patient's body, e.g., the abdominal wall. The inner ring 104 and the sleeve 106 are then manually inserted into body cavity 402 through the incision with the outer ring 102 remaining external to the body cavity 402. Once the inner ring 104 is within the body cavity 402, it expands around the inner surface of the incision so as to be generally parallel to the abdominal wall. The sleeve 106 provides a channel from the outside to the inside of the body cavity 402. The outer ring 102 initially rests above the abdominal wall around the wound opening 400. Since the upper end of the sleeve 106 is connected to the outer ring 102, the sleeve 106 can be drawn upwards and radially outward or inward, thereby drawing the inner ring 104 tightly against the inner surface of the abdominal wall. Moreover, the intermediate portion of the sleeve 106 is drawn tightly against the sides and edges of the wound opening 400, thereby retracting the adjacent tissue and producing a tightly sealed opening in the body cavity 402. That is, the sleeve 106 contacts the entire wound surface and protectively covers the same and seals it from contamination and infection. Depending on the size and depth of the incision, the user can roll up the sleeve 106 by gripping the double-tube outer ring 102 and turning it in a direction 200 as illustrated in FIGS. 2A-2C until the sleeve 106 abuts the outer edge of the wound opening 400. It should be appreciated that the outer ring 102 can be turned around its annular axis in either an outward or inward direction to roll the sleeve 106.

Figure 2D:
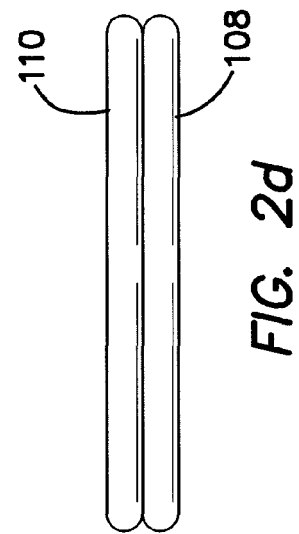

The outer ring 102 has a unique and novel double-tube configuration wherein through simple manipulation of forcing a first tube in a first direction and a second tube in a second direction, the positions of the first and second tubes can be inverted resulting in fast and easy turning of the tubes as illustrated in FIGS. 2A-2D. In one embodiment of the invention, the outer ring 102 is rotated by pushing the bottom tube or second circular tube 110 inward while pulling the top tube or first circular tube 108 outward (see FIG. 2A). The combination of the above steps results in inversion of the first and second circular tubes as illustrated in FIG. 2D. That is, the outer ring 102 can be rotated in 180° turns thereby retracting the sleeve 106. The above process can be repeated until a desired compression or wound opening is achieved.

An advantage of the invention is it provides for an easier, faster and higher retraction rate than that known in the prior art, thereby resulting in less traumatic effects to the patient. Another advantage of the invention is it provides tactile gripping and incremental rolling of the sleeve about the outer ring. In the above description, the first and second tubes of the outer ring are in a vertical position but it should be appreciated that the first and second tubes may be in different positions relative to one another such as a horizontal position.

In another embodiment of the invention, a small wire 302 such as a stainless steel wire is placed inside a lumen of the double-tube outer ring 102 (see FIGS. 3 and 10-13) so as to provide an audible signal as the outer ring 102 is turned. That is, as the double-tube outer ring 102 is turned, the wire 302 deflects against the tubing wall so as to provide an audible sound feedback to the user. Another feature of the wire 302 is it provides retraction stability to the wound retractor 100.

After surgery, the wound retractor 100 may be retrieved by grabbing the inner ring 104 and the sleeve 106 and pulling them through the wound opening 400. The use of the sleeve 106 and the ease of retracting the outer ring 102 provide higher compression between the inner and outer rings. As a result, the wound retractor 100 of the invention provides incremental adjustability to fit a wide range of incision sizes and isolates and protects the wound from bacterial infection as the diseased body parts and contaminated instruments are passed through the wound.

FIGS. 5-9 and 14-16 illustrate a wound retractor 500 having a roller design in accordance with another embodiment of the invention. The wound retractor 500 comprises an outer ring 502, an inner ring 504, and a distensible sleeve 506 connecting the outer ring 502 and the inner ring 504. The sleeve 506 can be attached to the outer ring 502 and the inner ring 504 by heat seal or adhesive. The outer ring 502 includes a hollow tube or lumen 508 that has a fan-like shape cross-section as illustrated in FIG. 5. The outer ring 502 further comprises an inner rod 510 that has a similar fan-like geometry on its outer surface as illustrated in FIG. 6. The hollow tube 508 and the inner rod 510 are coaxially joined to form the outer ring 502 of the wound retractor 500.

Figure 8:
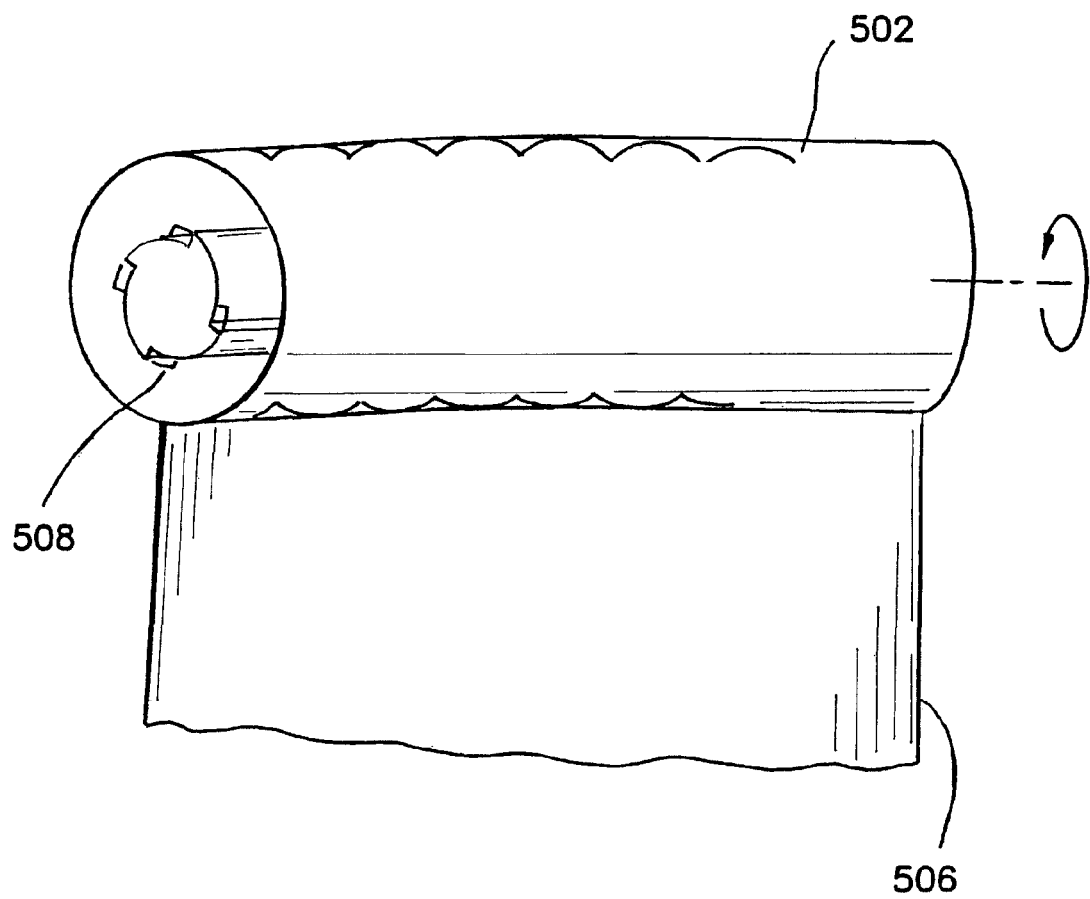
FIG. 8 illustrates the retraction and alignment of the outer ring to fit a desired incision size in accordance with the second embodiment of the invention.

The fan-like geometry of the outer ring 502 serves as an incremental rotating mechanism. In particular, when the hollow tube 508 is manually rolled out of its coaxial alignment with respect to the inner rod 510, the hollow tube 508 will index itself until it matches the next alignment point of the inner rod 510 as illustrated in FIG. 8. When the hollow tube 508 and the inner rod 510 are coaxially aligned, they lock in place preventing further indexing until the steps of retracting are repeated. It is appreciated that each of the hollow tube 508 and the inner rod 510 has at least one alignment point providing indexing and incremental rotation of the outer ring 502. That is, the outer ring 502 can incrementally retract in steps based on the number of alignment points or indexes on the fan.

Figure 9:
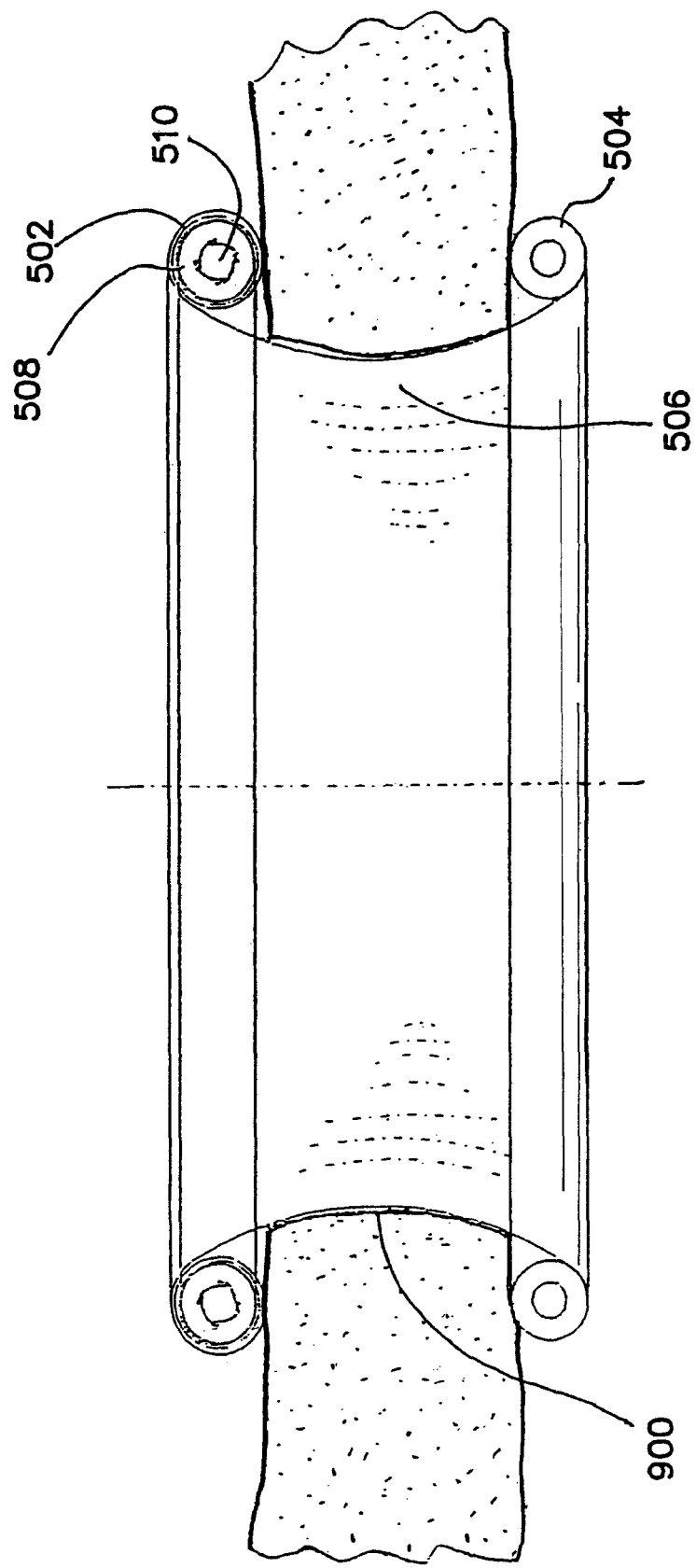
FIG. 9 illustrates the wound retractor of FIG. 7 installed in an incision.
Figure 13:
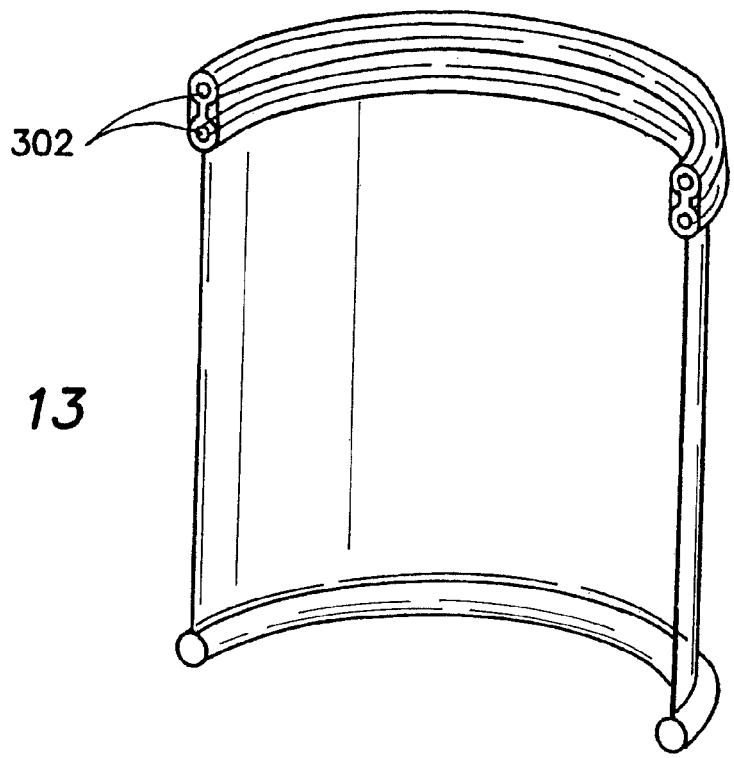
FIG. 13 is a three-dimensional cross-section view of the wound retractor of FIG. 10.
Figure 14:
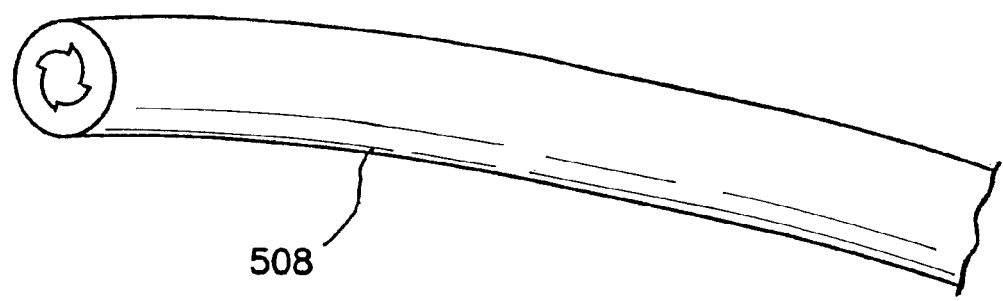
FIG. 14 is a three-dimensional image of the hollow tube of the outer ring of the wound retractor in accordance with the second embodiment of the invention.
Figure 15:
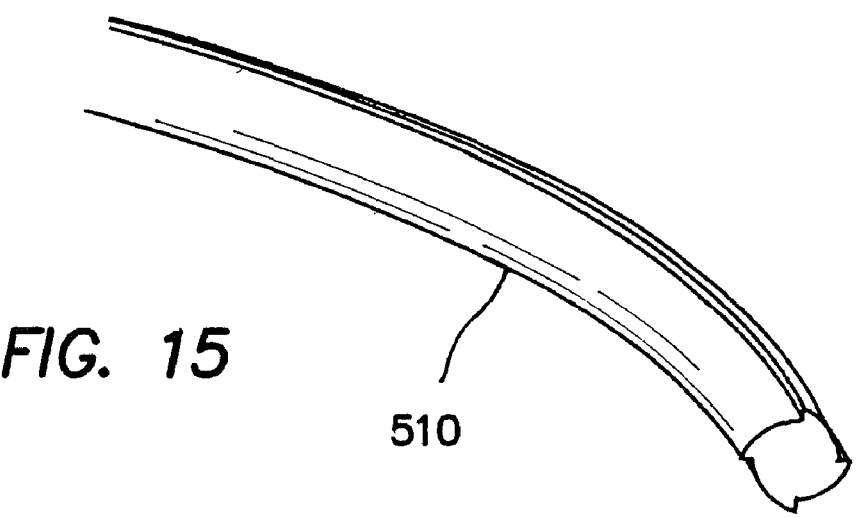
FIG. 15 is a three-dimensional image of the inner rod of the outer ring of the wound retractor in accordance with the second embodiment of the invention.
Figure 16:
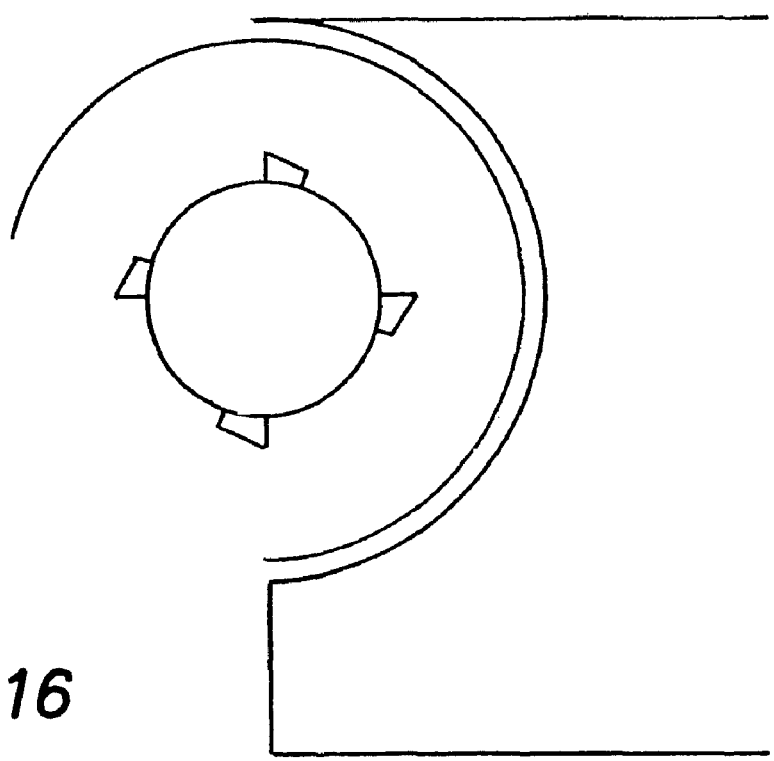
FIG. 16 is a cross-section view of the hollow tube and inner rod coaxially joined in accordance with the second embodiment of the invention.
Figure 17B:
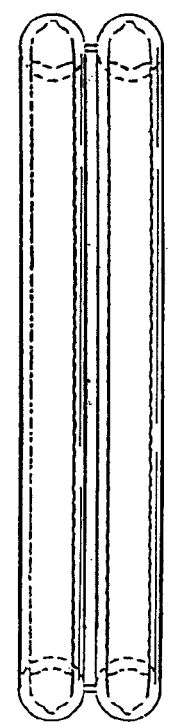
FIGS. 17A-17E illustrate cross-section views of additional embodiments of the outer ring of the invention.
Figure 17C:
Figure 17A:
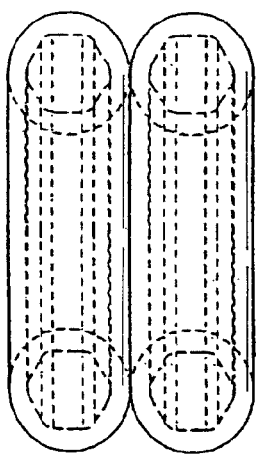
Figure 17E:
Figure 17D:
Figure 18A:
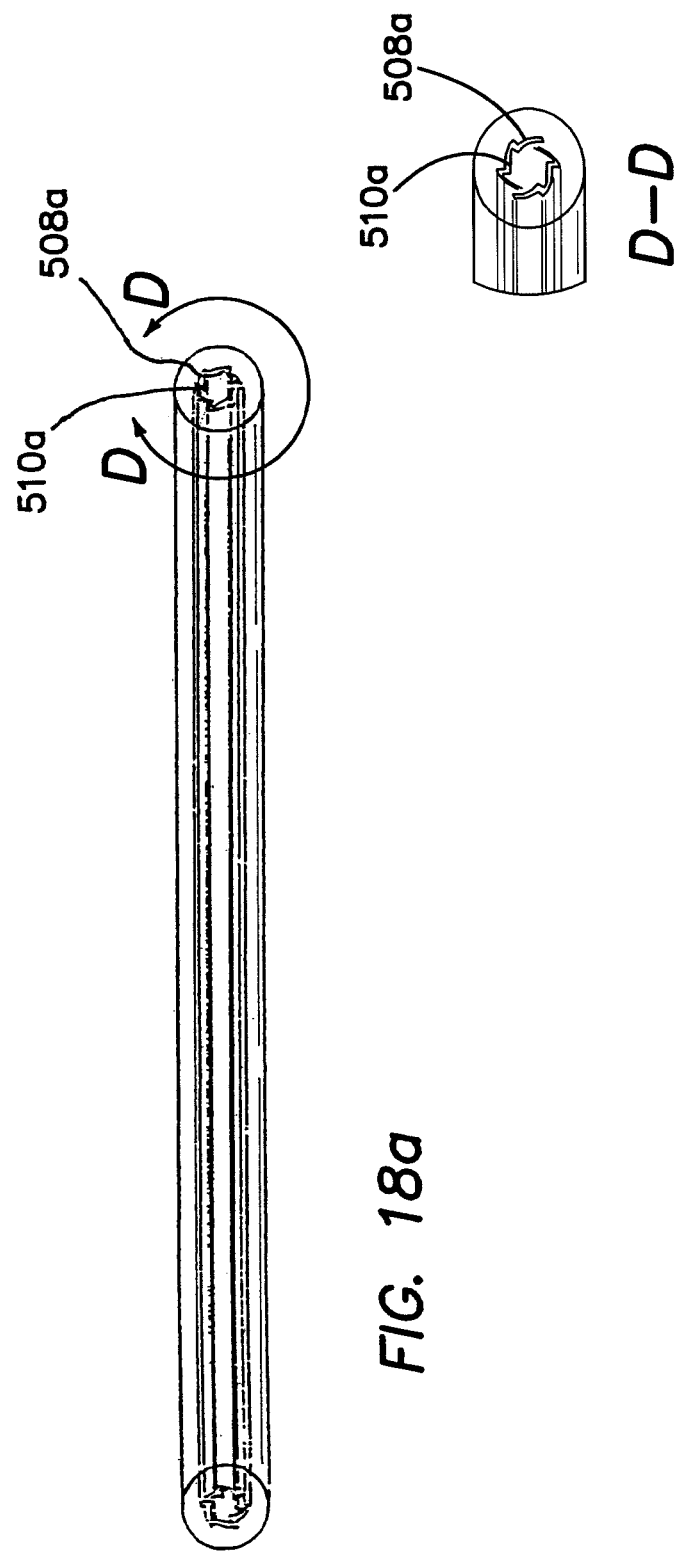

FIG. 9 illustrates a process of installing the wound retractor 500 in a wound opening 900. An incision in the shape of a slit is first made in a patient's body, e.g., the abdominal wall. The inner ring 504 and the sleeve 506 are then manually inserted and positioned underneath and along the edges of body cavity wall 512, and the outer ring 502 is pulled through the wound opening 900 so as to be placed outside the body cavity wall 512. Retraction of the sleeve 506 can then be achieved by rolling the outer ring 502 over the sleeve 506 in a direction 700 as shown in FIG. 7 until a desired compression or wound opening is achieved. Incremental retraction is achieved by manually rolling the hollow tube 508 out of its coaxial alignment with the inner rod 510, i.e., the hollow tube 508 can be rolled and indexed to match the next alignment point between the hollow tube 508 and the inner rod 510.

When the hollow tube 508 and the inner rod 510 are coaxially aligned, they lock in place preventing further indexing until the outer ring 502 is rolled out of its alignment again. This process is repeated until a desired retraction is achieved. Once surgery is complete, the wound retractor 500 can be retrieved by grabbing the inner ring 504 and the sleeve 506 and pulling them through the wound opening 900.

It is appreciated that the outer ring can be designed in various shapes and sizes to achieve various retraction rates and/or to conform with different body surfaces as illustrated in FIGS. 17A-17E. For example, the outer ring may comprise a single or multiple tubes of different shapes and sizes. The single or multiple tubes may be solid or include lumens of different shapes and sizes.

Similarly, the wound retractor having the roller design could be of various geometries. As illustrated in FIGS. 18A-18L, hollow tubes 508a-508l and inner rods 510a-510l, respectively, of the outer ring may have different shapes and sizes and may contain multiple locking mechanisms. For example, the inner rods 510b-510e and 510l have solid rectangular cross-sections. In comparison, the inner rods 510f-510k have hollow circular cross-sections. The hollow tubes and inner rods may be made of the same or different materials (e.g., soft and/or hard). For example, the inner rods may be rigid such as a wire or piece of metal, or they may be flexible such as an extension spring. The lumens of the hollow tubes 508a-508l may have cross-sections of different geometries such as fan-like geometry, circular, oval, circular with lumps, triangular, rectangular, any geometric shape with multiple sides, etc. Advantages of the above embodiments of the invention include improved retraction adjustability and stability.

Figure 19C:
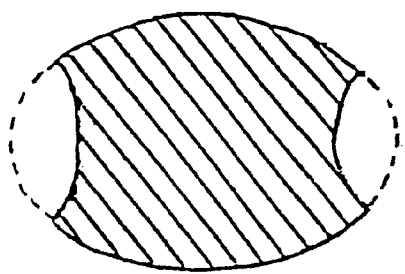
Figure 19D:
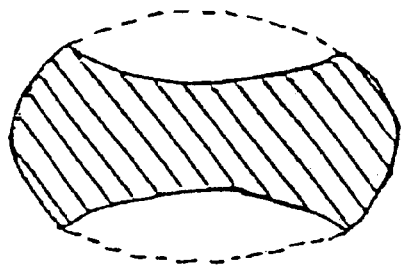
Figure 19E:
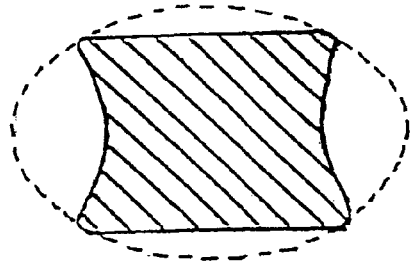
Figure 19G:
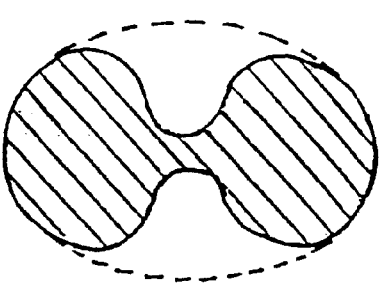
Figure 19F:
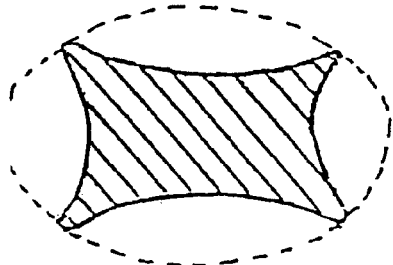
Figure 20B:
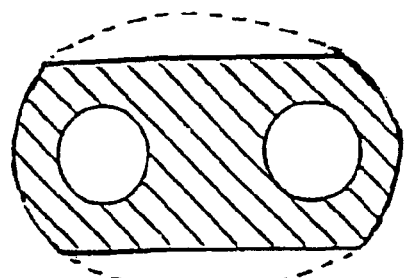
FIGS. 20A-20G illustrate cross-section views of additional embodiments of the outer ring of the invention having generally prolate cross-sections and including lumens.
Figure 20A:
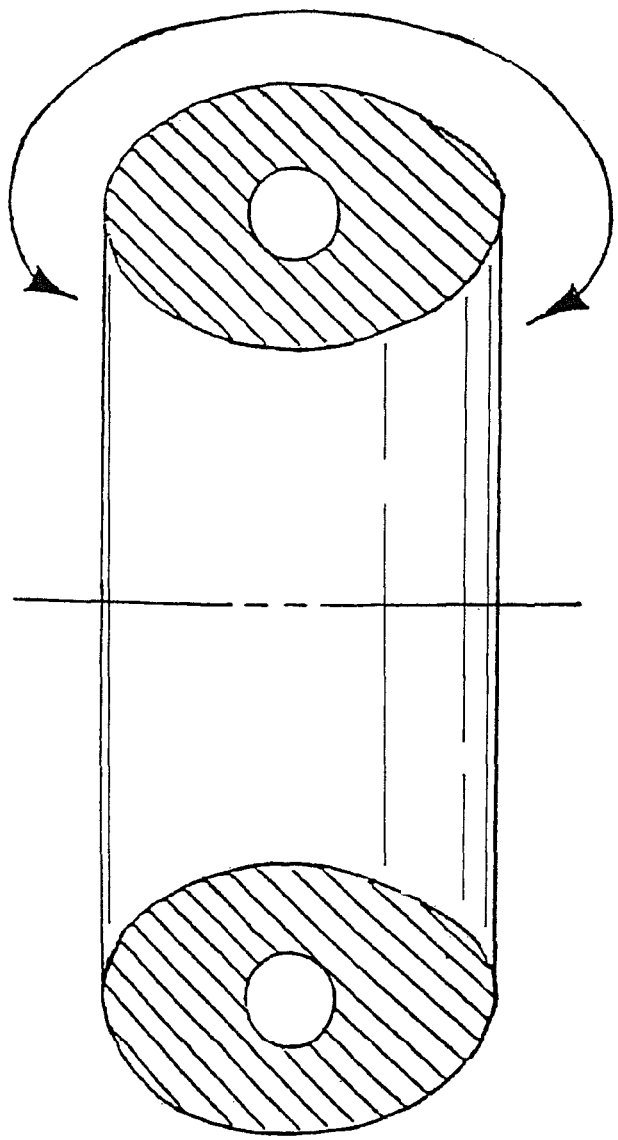
Figure 20C:
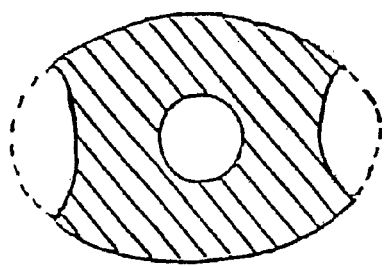
Figure 20D:
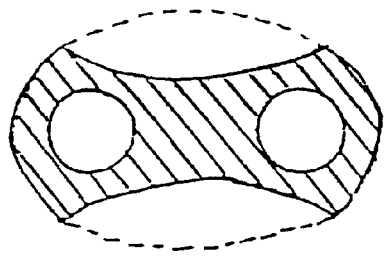
Figure 20E:
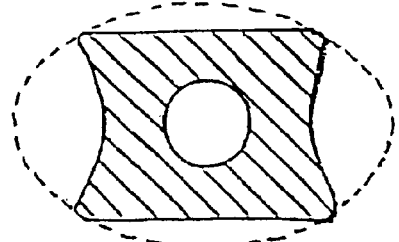
Figure 20F:
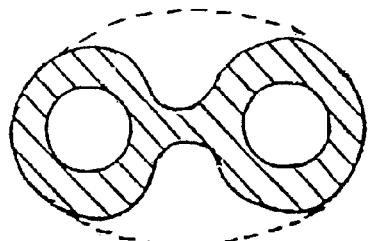
Figure 20G:
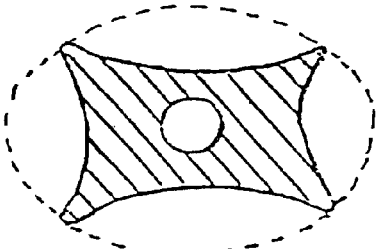

FIGS. 19A-19G illustrate cross-section views of additional embodiments of the outer ring of the invention having generally prolate cross-sections. That is, the longer axis of the cross-section of the outer ring is generally parallel to axis E-E as illustrated in FIG. 19A. The outer ring can be turned around the axis E-E in either an outward or inward direction 800 to roll up the sleeve (not shown). The outer rings of FIGS. 19A-19G provide tactile gripping and incremental rolling of the sleeve about the rings. FIG. 19B illustrates an outer ring 190 having two straight chordal surfaces 190a and 190b that are generally parallel to the axis E-E. FIG. 19C illustrates an outer ring having two straight chordal surfaces and two curved chordal surfaces. FIGS. 19D-19G illustrate outer rings having at least two curved chordal surfaces.

FIGS. 20A-20G illustrate cross-section views of the outer rings of FIGS. 19A-19G, respectively, further including at least one lumen in each ring. The lumen may house an inner rod (not shown) that deflects against the lumen wall providing an audible feedback to the user. The lumen and inner rod may be of different geometries and sizes.

Figure 21A:
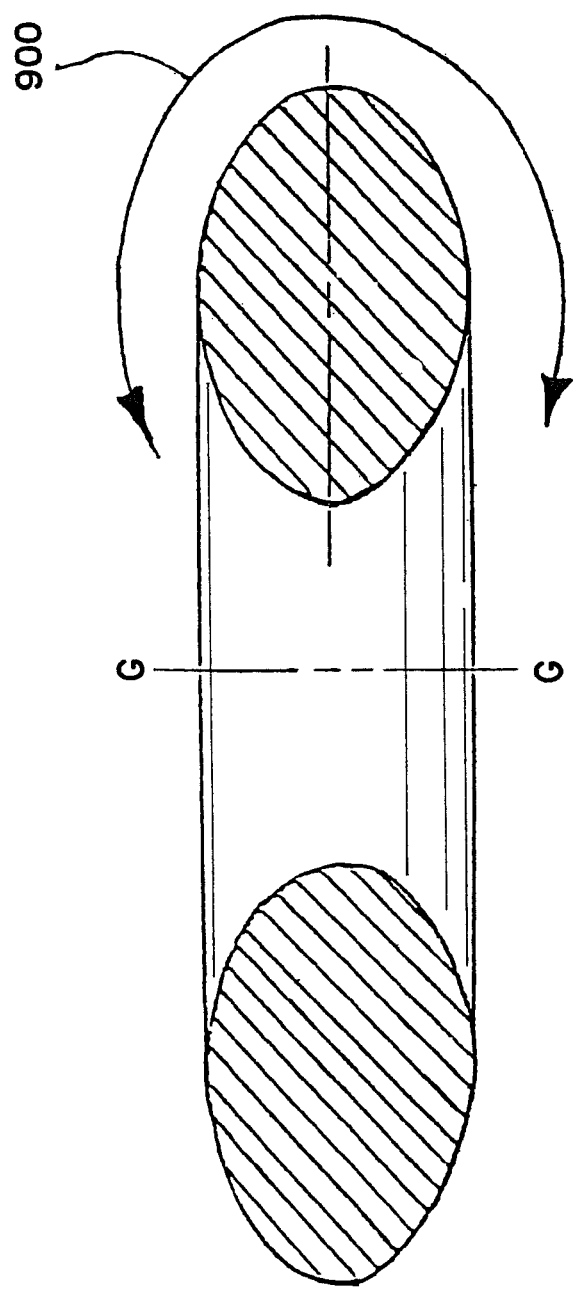
FIGS. 21A-21E illustrate cross-section views of additional embodiments of the outer ring of the invention having generally oblate cross-sections.
Figure 21B:
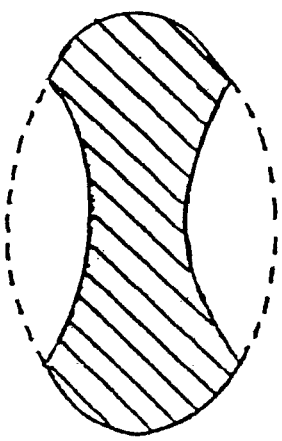
Figure 21C:
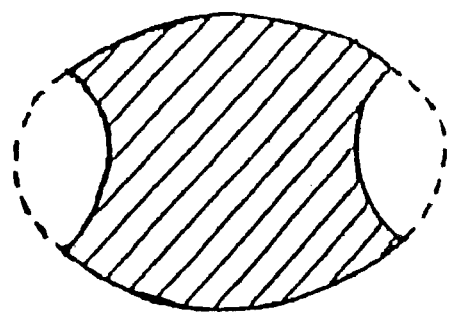
Figure 21D:
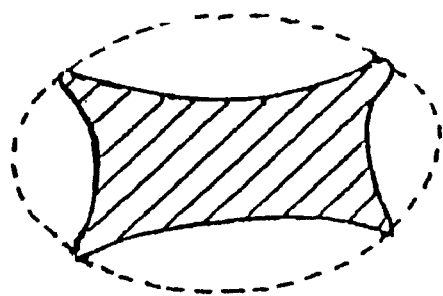
Figure 21E:
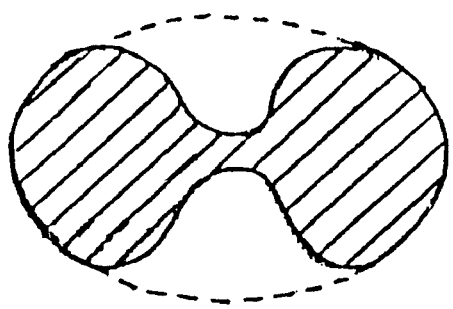
Figure 22A:
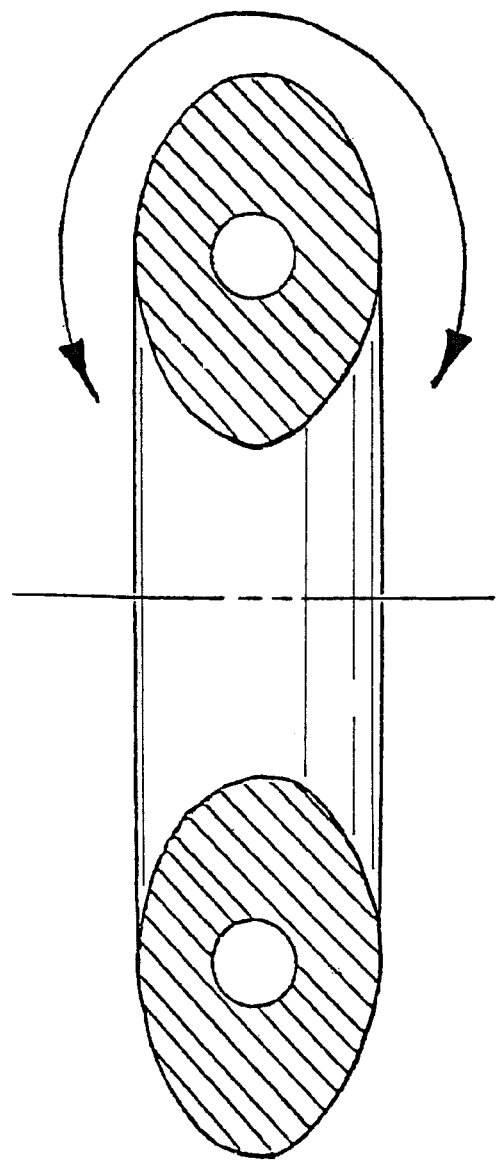
FIGS. 22A-22E illustrate cross-section views of additional embodiments of the outer ring of the invention having generally oblate cross-sections and including lumens.
Figure 22B:
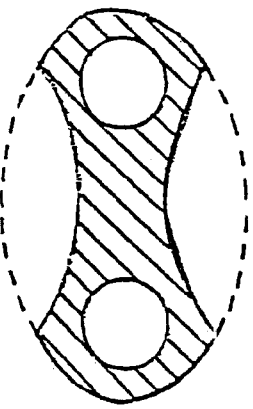
Figure 22C:
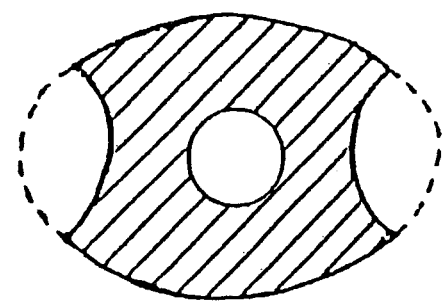
Figure 22D:
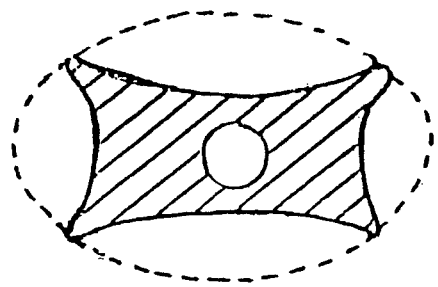
Figure 22E:
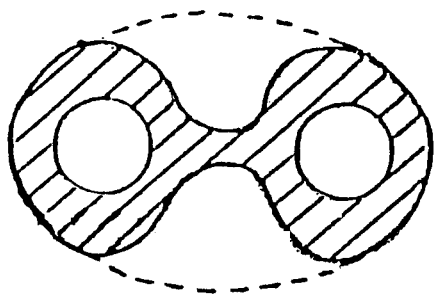

FIGS. 21A-21E illustrate cross-section views of additional embodiments of the outer ring of the invention having generally oblate cross-sections. That is, the longer axis of the cross-section of the outer ring is generally perpendicular to axis G-G as illustrated in FIG. 21A. The outer ring can be turned around the axis G-G in either an outward or inward direction 900 to roll up the sleeve (not shown). The outer rings of FIGS. 21A-21E provide tactile gripping and incremental rolling of the sleeve about the rings. FIGS. 21B-21E illustrate outer rings having at least two curved chordal surfaces.

FIGS. 22A-22E illustrate cross-section views of the outer rings of FIGS. 21A-21E, respectively, further including at least one lumen in each ring. The lumen may house an inner rod (not shown) that deflects against the lumen wall providing an audible feedback to the user. The lumen and inner rod may be of different geometries and sizes.

Figure 23A:
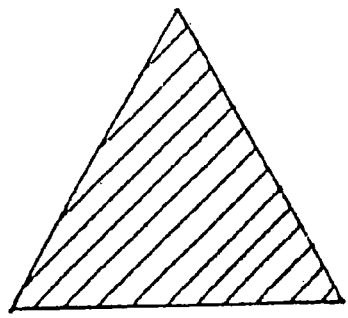
FIG. 23A illustrates a cross-section view of another embodiment of the outer ring of the invention having a triangular cross-section.
Figure 23B:
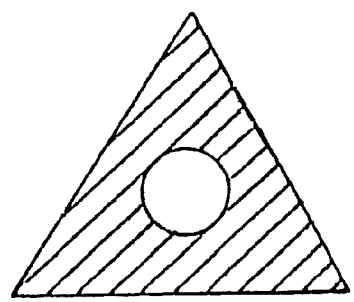
FIG. 23B illustrates a cross-section view of the outer ring of FIG. 23A further including a lumen.
Figure 24A:
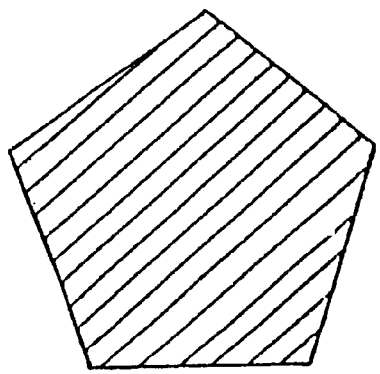
FIG. 24A illustrates a cross-section view of another embodiment of the outer ring of the invention having a cross-section comprising an odd number of sides such as a pentagon.
Figure 24B:
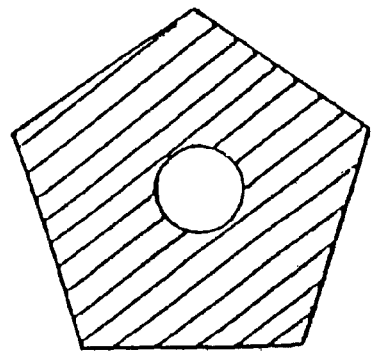
FIG. 24B illustrates a cross-section view of the outer ring of FIG. 24A further including a lumen.

FIG. 23A illustrates a cross-section view of another embodiment of the outer ring of the invention having a triangular cross-section, and FIG. 23B illustrates a cross-section view of the outer ring of FIG. 23A further including a lumen. In another embodiment of the invention, FIG. 24A illustrates a cross-section view of the outer ring of the invention having an odd number of sides such as a pentagon, and FIG. 24B illustrates a cross-section view of the outer ring of FIG. 24A further including a lumen. These outer rings provide tactile gripping and incremental rolling of the sleeve about the rings. The lumens of the outer rings in FIGS. 23B and 24B may be of different shapes and sizes to house inner rods (not shown) having different shapes and sizes. It is appreciated that the outer ring can be designed in various shapes and sizes to achieve various retraction rates and/or to conform with different body shapes.

Figure 25A:
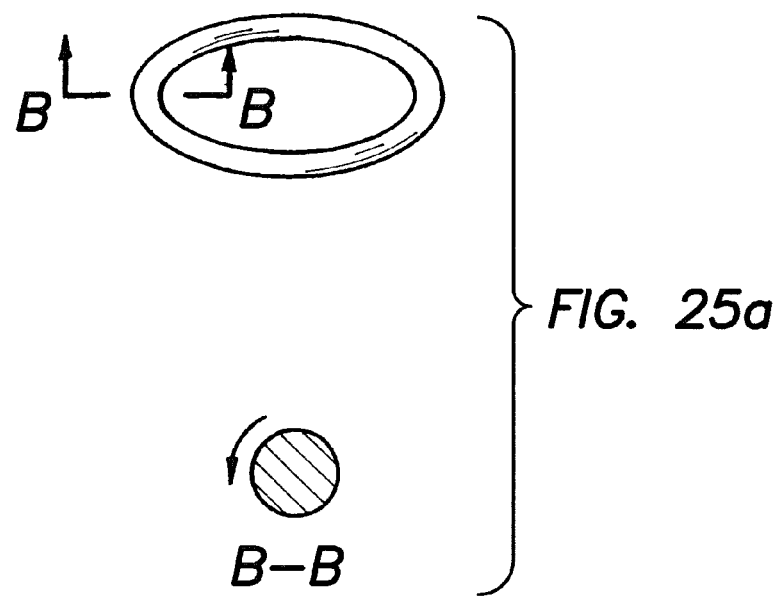
FIGS. 25A-25B illustrate different processes of forming the outer ring of the invention.
Figure 25B:
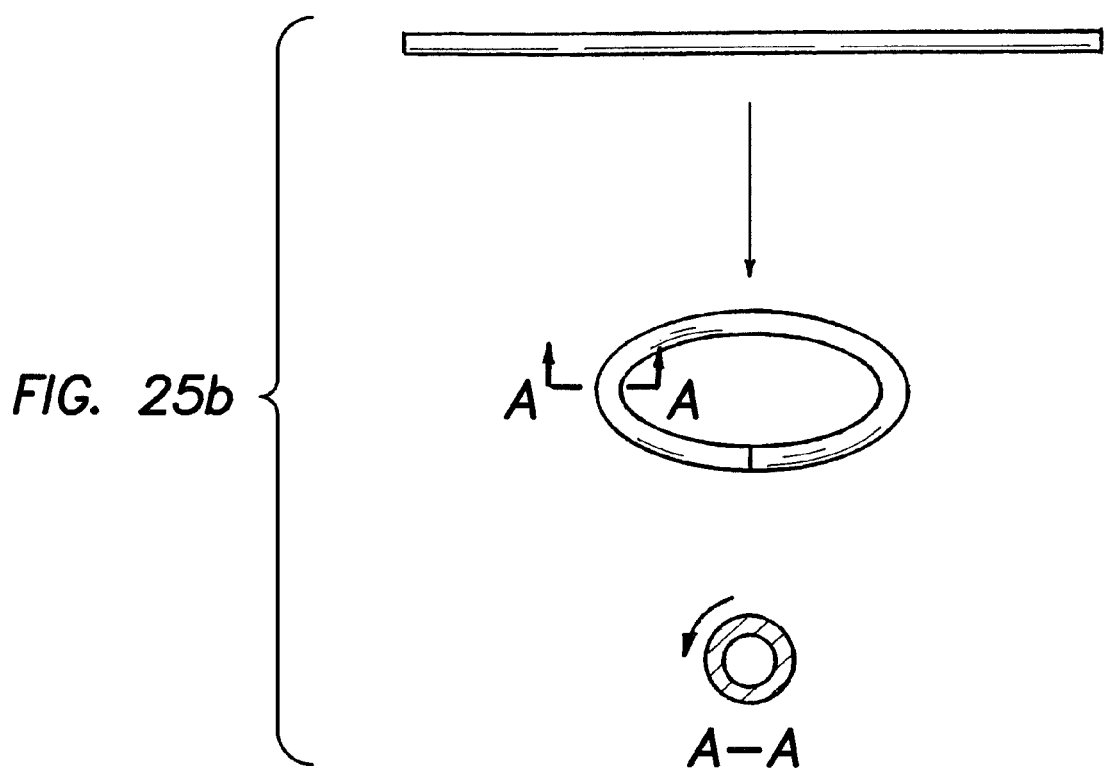

FIGS. 25A-25B illustrate different processes of forming the outer ring of the invention. The outer ring, which may be solid or include a lumen, may be molded as a circular ring as shown in FIG. 25A, or the outer ring may be formed by joining a single or multiple extruded tubes into a circular ring as shown in FIG. 25B.

In another embodiment of the invention, access into and out of a patient's body is achieved by a hand assisted laparoscopic (HAL) procedure using a surgical access device such as the Gelport™ device as described in applicant's international application PCT/US01/29682, filed on Sep. 21, 2001, entitled "Surgical Access Apparatus and Method," which is incorporated herein by reference, while retraction is provided by the wound retractor of the present invention. The purpose of this embodiment is to combine the features and advantages of both the wound retractor of the present invention and the surgical access device as described in the PCT application. As explained in the PCT application, the current surgical access device uses a polyisoprene sheath that is wrapped distally around an O-ring, and once placed into a wound incision, the sheath is then stretched over extended tabs onto an abdominal base. The sheath of the surgical access device requires stretching and often times requires multiple attempts to secure it to the abdominal base. A novelty of this embodiment is to modify the cap and/or the abdominal base of the surgical access device so that it will accept the wound retractor of the present invention to replace the polyisoprene sheath and to maintain an airtight seal. The use of the wound retractor would simplify the HAL procedure and would not require stretching.

Figure 26:
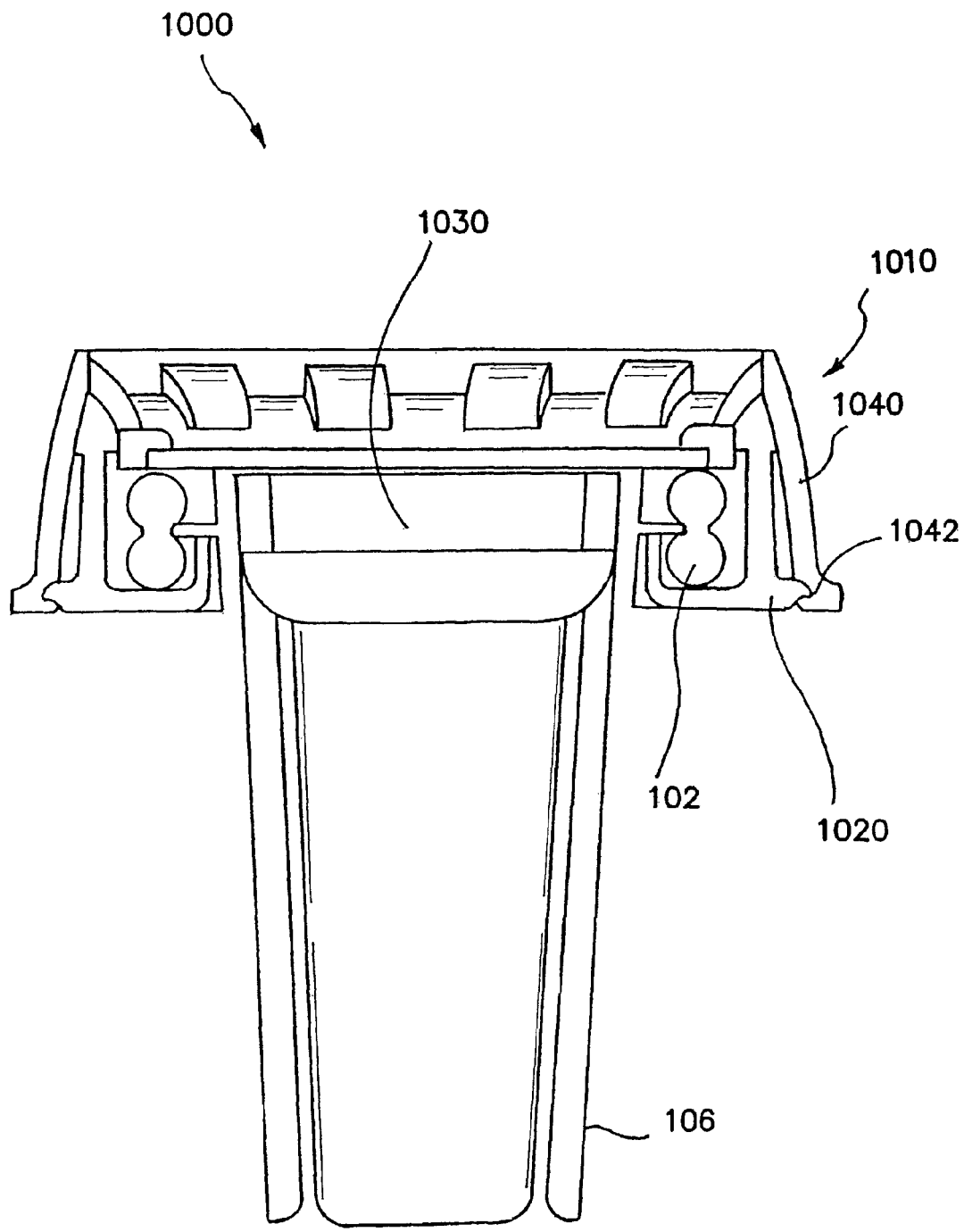
FIG. 26 illustrates an axial cross-section view of a surgical access device with a slightly modified gel cap and/or abdominal base in accordance with another embodiment of the invention.
Figure 27:
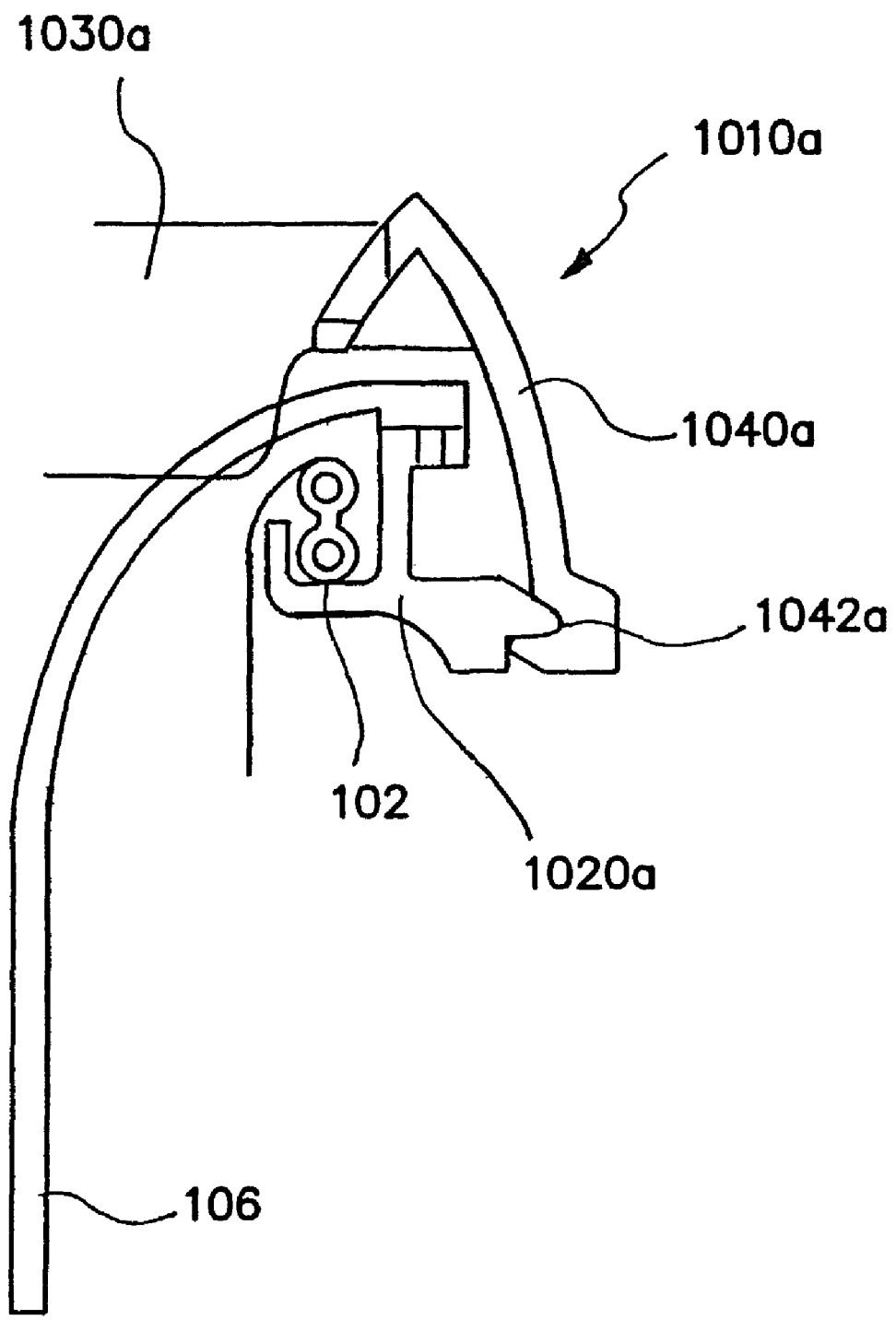
FIG. 27 is an axial cross-section view of a surgical access device in accordance with another embodiment of the invention.
Figure 28:
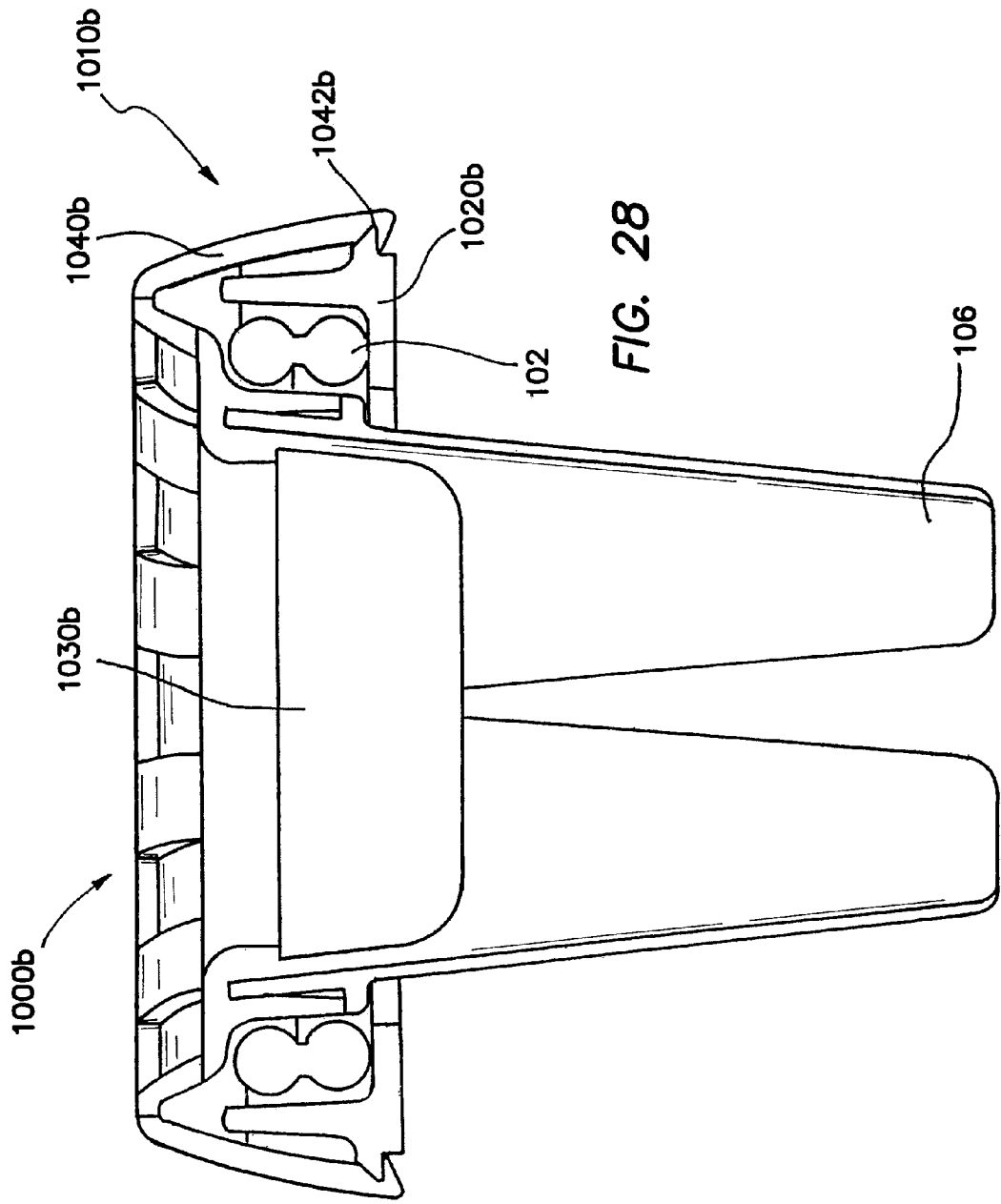
FIGS. 28-30 illustrate additional exemplary embodiments of the invention having modifications that could be made to the gel cap and/or the abdominal base so that the surgical access device can be used with the wound retractor.
Figure 29:
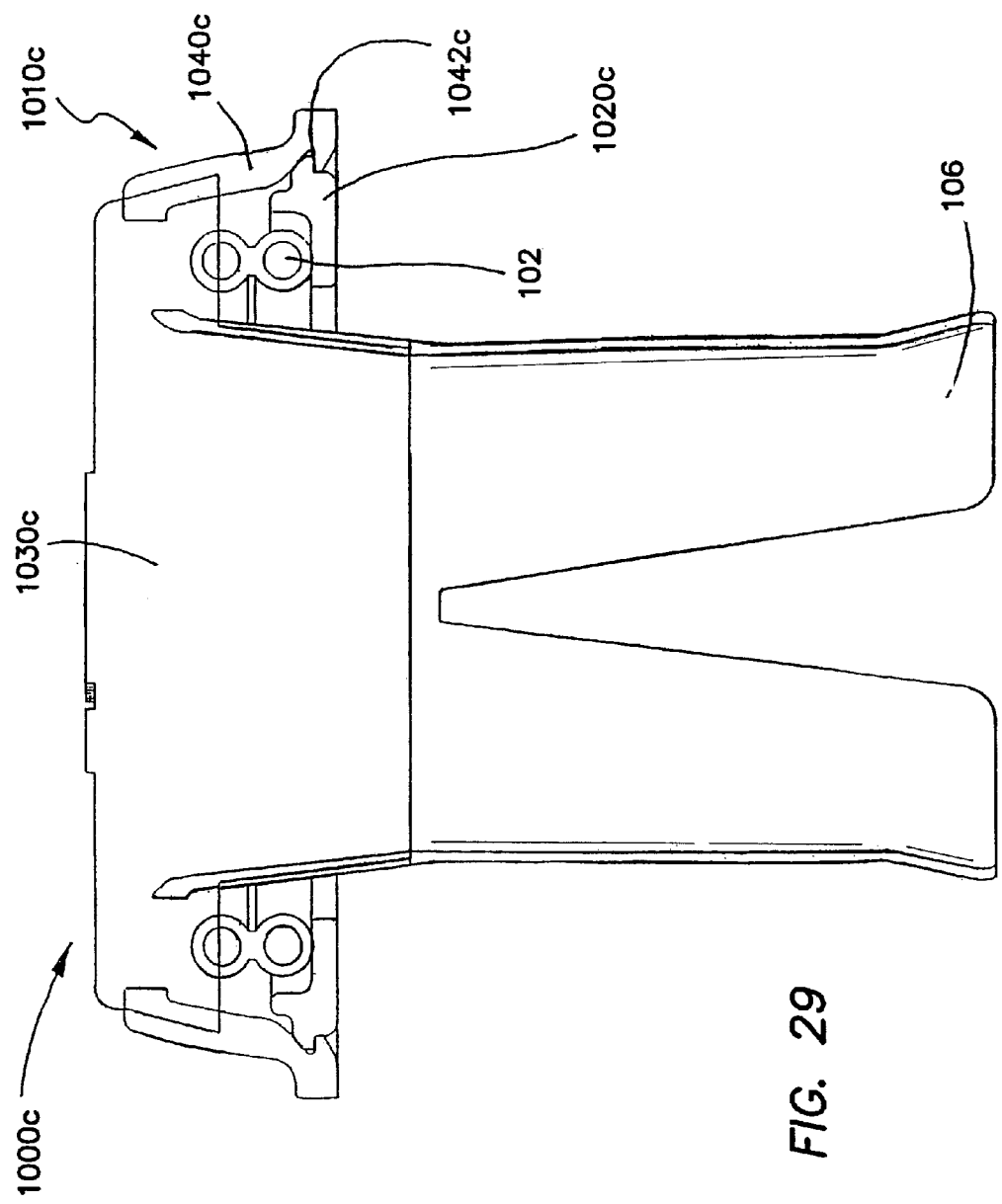
Figure 30:
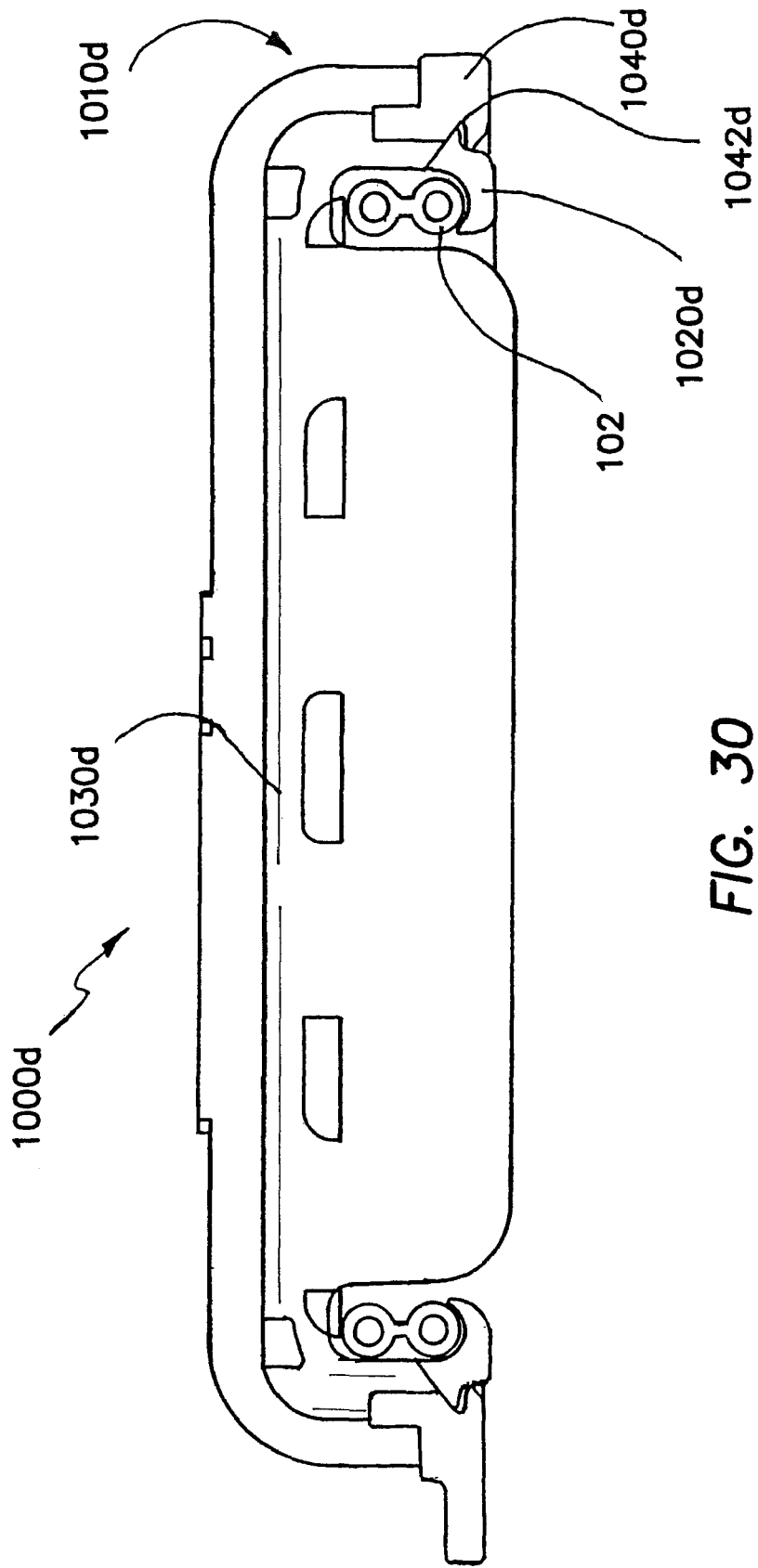

Referring to FIG. 26, there is shown a surgical access device 1000 with slight or moderate modifications to a gel cap 1010 and to an abdominal base 1020. The gel cap 1010 further includes a gel pad 1030 and a circumferential cap ring 1040, which can be inserted and molded to the pad 1030. The resulting gel cap 1010 forms a seal with the base 1020, thereby defining a working channel through the pad 1030, the cap ring 1040, the base 1020, and the sleeve 106 of the wound retractor. In this manner, the working channel includes a single valve formed by the gel pad 1030 which provides both a zero seal and an instrument seal for a wide range of instrument diameters. Referring to FIG. 27, the cross-section view of gel cap 1010a illustrates an annular void 1042a that is formed on the inner circumference of cap ring 1040a. This void is of particular advantage in forming a sealing relationship with base 1020a. FIGS. 28-30 illustrate additional exemplary embodiments of the invention having modifications that could be made to the gel cap and/or the abdominal base so that the surgical access device can be used with the wound retractor.

Figure 31:
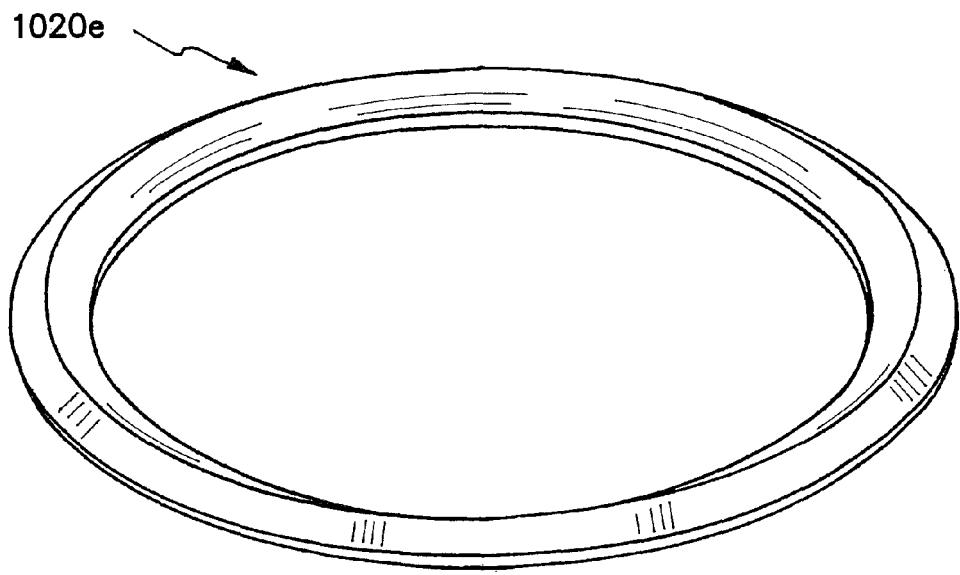
FIG. 31 illustrates a perspective view of a base of a surgical access device in accordance with another embodiment of the invention.
Figure 32:
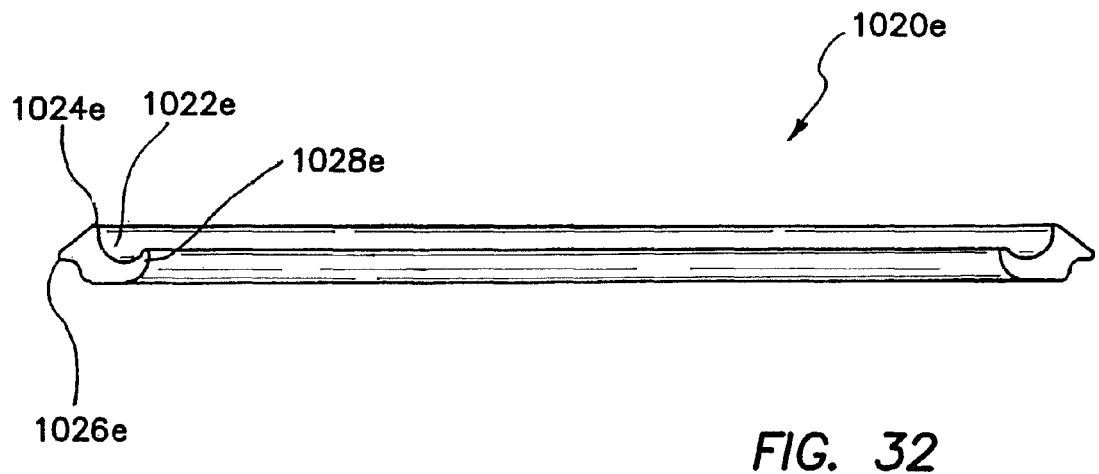
FIG. 32 is an axial cross-section view of the embodiment illustrated in FIG. 31.

FIG. 31 illustrates a perspective view of a base 1020e in accordance with another embodiment of the invention. FIG. 32 is an axial cross-section view of the embodiment illustrated in FIG. 31. From these views, it will be noted that the base 1020e can be provided with a smooth generally cylindrical inner surface 1022e which extends proximally to a rounded end surface 1024e and outwardly from the end surface 1024e along an annular lip 1026e, which is sized and configured to fit into an annular void formed on the inner circumference of a corresponding cap ring. Proximally of the inner surface 1022e, the base 1020e can also include a rounded end surface 1028e along its inner diameter for securing the outer ring of the wound retractor once the sleeve has been shortened.

Figure 33:
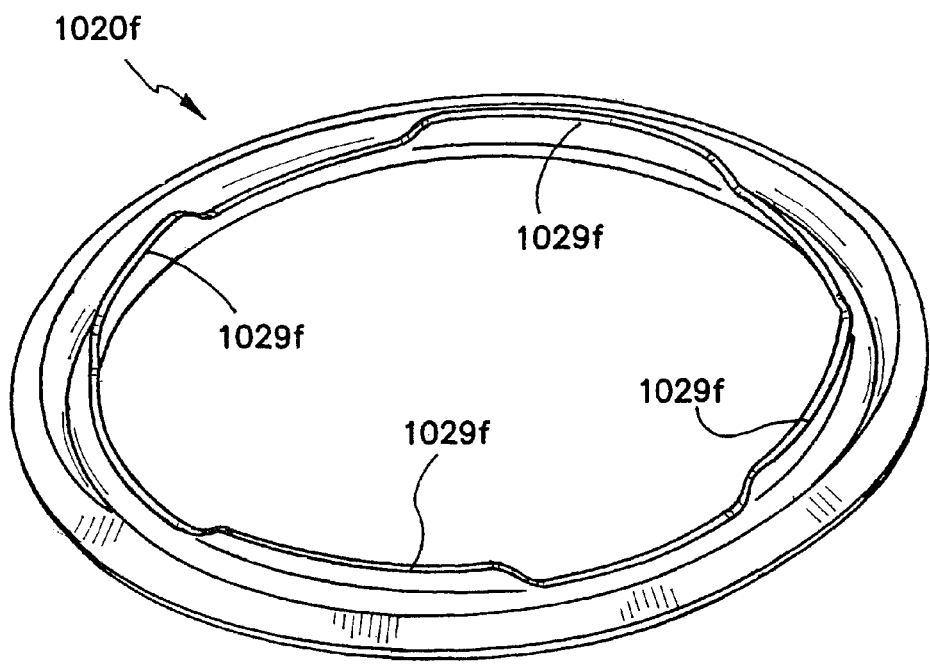
FIGS. 33 and 34 illustrate a base of a surgical access device in accordance with another embodiment of the invention having at least one toggle or latch adapted to fit a corresponding cap ring.
Figure 34:
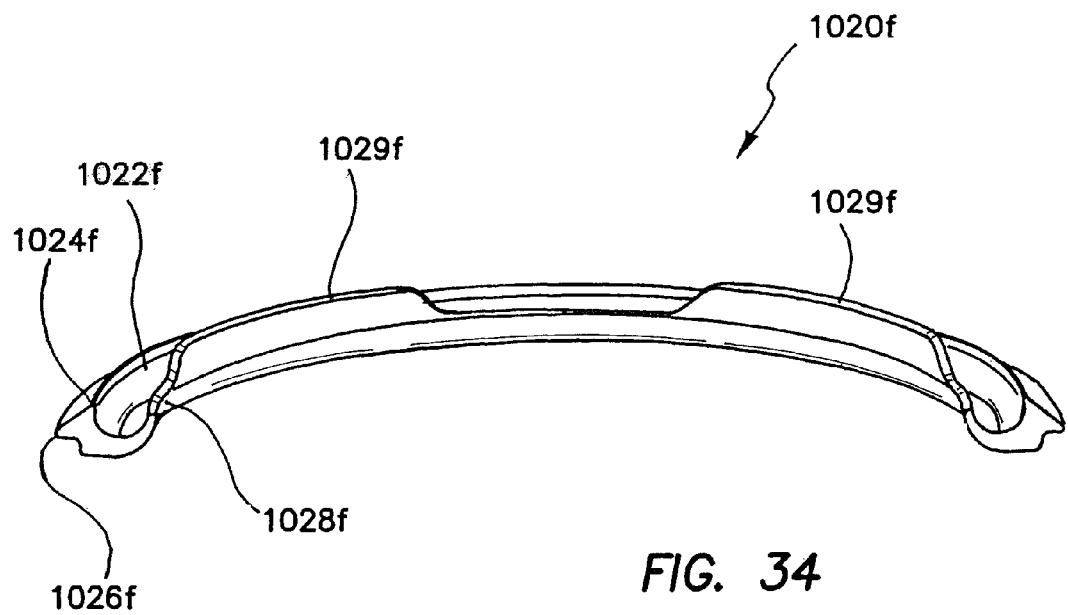
Figure 35:
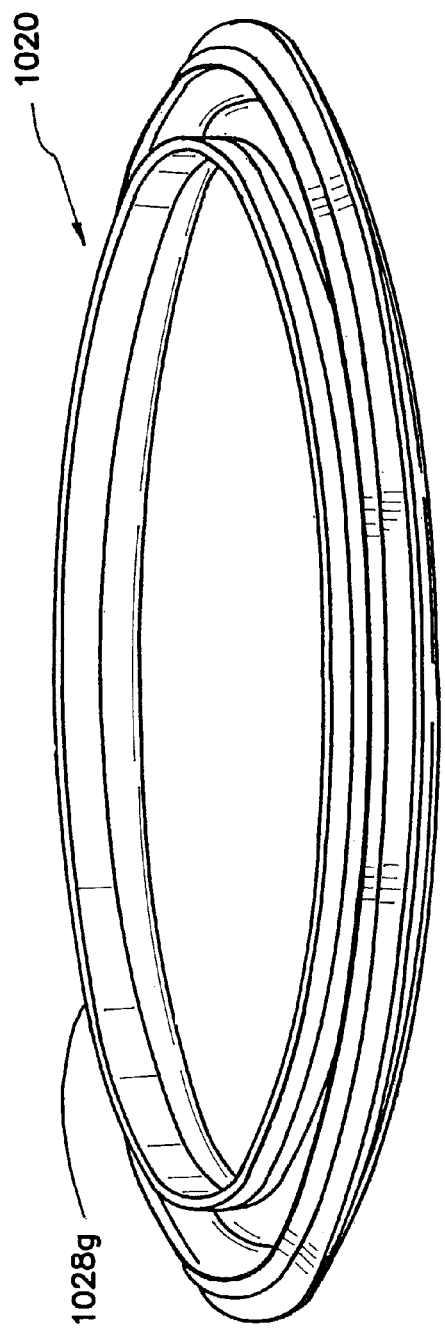
FIGS. 35 and 36 illustrate a base of a surgical access device in accordance with another embodiment of the invention having a raised wall on an inner diameter and adapted to fit a corresponding cap ring.
Figure 36:
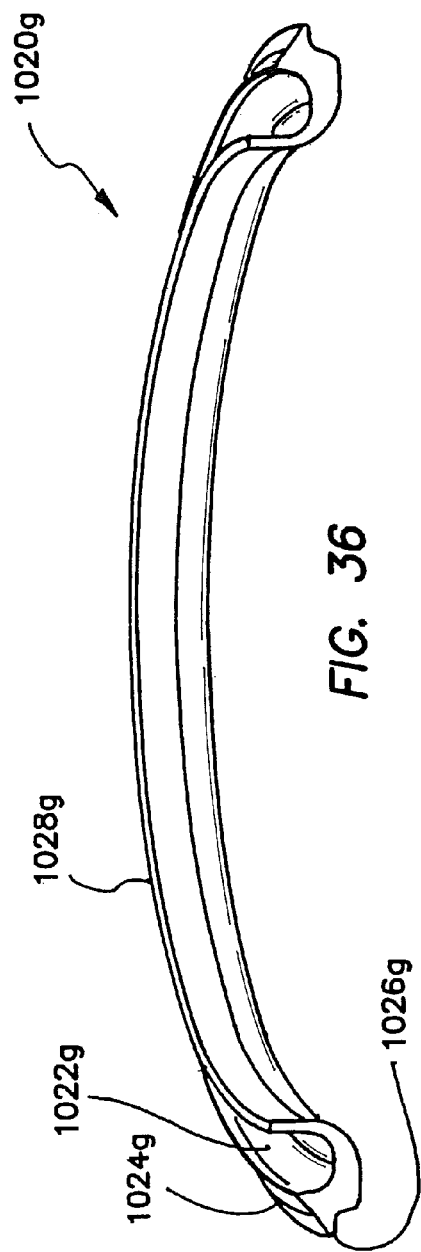

In another embodiment of the invention, FIGS. 33 and 34 illustrate a base 1020f having a smooth generally cylindrical inner surface 1022f, a rounded end surface 1024f, an annular lip 1026f, and an end surface 1028f having at least one toggle or latch 1029f sized and configured to fit a corresponding cap ring. In this embodiment, the toggle or latch 1029f operates to change the inner diameter of the cap ring to create a seal or release the cap ring from the base. In yet another embodiment of the invention, FIGS. 35 and 36 illustrate a base 1020g having a smooth generally cylindrical inner surface 1022g, a rounded end surface 1024g, an annular lip 1026g, and an end surface 1028g having a raised wall sized and configured to fit a corresponding cap ring.

An advantage associated with the modified surgical access device is it enables a surgeon to quickly retract and protectively line an abdominal wall incision while being able to easily accommodate variations from patient to patient in the thickness of the abdominal wall. In addition, the device effectively seals around the interior and exterior of the incision, and allows a sealing cap to be attached to seal the abdominal cavity and to enable a laparoscopic procedure to be performed.

Many alterations and modifications may be made by those having ordinary skill in the art without departing from the spirit and scope of the invention. For these reasons, the above description should not be construed as limiting the invention, but should be interpreted as merely exemplary of preferred embodiments.

While certain embodiments have been particularly shown and described with reference to exemplary embodiments thereof, it will be understood by those of ordinary skill in the art that various changes in form and details may be made therein without departing from the spirit and scope thereof as defined by the following claims.

What is claimed is:

1. An adjustable wound retractor adapted to dilate a surgical wound incision to a desired diameter, comprising:
    a first ring having a diameter greater than the desired diameter of the wound incision and being adapted for disposition interiorly of the wound incision;
    a second ring having a lumen having a tubing wall and a diameter greater than the desired diameter of the wound incision and being adapted for disposition exteriorly of the wound incision;
    a rod disposed inside the lumen, and
    a flexible sleeve disposed in a generally cylindrical form between the first ring and the second ring.

2. The wound retractor of claim 1, wherein the rod is a stainless steel wire.

3. The wound retractor of claim 1, further comprising a valve structure disposed relative to the incision to securely receive the second ring.

4. The wound retractor of claim 3, wherein the valve structure comprises a gel cap and an abdominal base.

5. An adjustable wound retractor adapted to dilate a surgical wound incision to a desired diameter, comprising:
    a first ring having a diameter greater than the desired diameter of the wound incision and being adapted for disposition interiorly of the wound incision;
    a second ring having a diameter greater than the desired diameter of the wound incision and being adapted for disposition exteriorly of the wound incision, the second ring having a lumen and a rod disposed within the lumen; and
    a flexible sleeve disposed in a generally cylindrical form between the first ring and the second ring;

wherein the second ring includes surfaces that are easy to grip and turn, allowing the user to roll the ring over itself to provide the sleeve with a radial retraction force sufficient to stretch the incision to the desired diameter.

6. The wound protector of claim 5, wherein the second ring comprises at least one curved chordal surface.

7. The wound retractor of claim 6, wherein the second ring further comprises at least one generally straight chordal surface.

8. The wound retractor of claim 5, wherein the second ring has a generally prolate cross-section.

9. The wound retractor of claim 5, wherein the second ring has a generally oblate cross-section.

10. The wound retractor of claim 5, wherein the lumen of the second ring has a cross-section including circular, oval, circular with at least one lump, rectangular, triangular, and any geometric shape with multiple sides.

11. The wound retractor of claim 5, wherein the second ring comprises two opposing curved chordal surfaces.

12. The wound retractor of claim 5, wherein the rod is a stainless steel wire.

13. The wound retractor of claim 5, wherein the rod has a cross-section including solid rectangular, hollow rectangular, solid circular, hollow circular, and any solid or hollow geometric shape.

14. An adjustable wound protector adapted to protect a surgical wound incision, comprising:
   a first ring having a diameter greater than the desired diameter of the wound incision and being adapted for disposition interiorly of the wound incision;
   a second ring having and a diameter greater than the desired diameter of the wound incision and being adapted for disposition exteriorly of the wound incision, the second ring having a lumen and a rod disposed within the lumen; and
   a flexible sleeve disposed in a generally cylindrical form between the first ring and the second ring, wherein the sleeve comprises a material impermeable to bacteria.

15. The wound protector of claim 14, wherein the sleeve material is impermeable to fluids.

16. The wound protector of claims 14, wherein the second ring may be rolled over itself to provide the sleeve with a radial retraction force sufficient to seal the protector against the edges of the wound incision.

17. The wound protector of claim 14, wherein the lumen has a fan-like shape cross-section.

18. The wound protector of claim 17, wherein the rod has a fan-like cross-section and is coaxially placed inside the lumen to serve as an incremental rotating mechanism of the wound retractor.

19. The wound protector of claim 14, wherein each of the tubing wall and the rod includes a plurality of alignment points that operate to index and match each other as the second ring is rolled out of and into alignment with respect to the rod.

20. The wound protector of claim 14, wherein each of the tubing wall and the rod includes at least one alignment point providing indexing and incremental rotation of the second ring.

* * * * *